(12) United States Patent
Varan et al.

(10) Patent No.: US 11,483,593 B2
(45) Date of Patent: Oct. 25, 2022

(54) SYSTEM FOR PROVIDING A VIRTUAL FOCUS GROUP FACILITY

(71) Applicant: Smart Science Technology, LLC, Austin, TX (US)

(72) Inventors: Duane Varan, Austin, TX (US); Erik Marc Johnson, Austin, TX (US); Michael Ross Menegay, Austin, TX (US)

(73) Assignee: Smart Science Technology, LLC, Austin, TX (US)

( * ) Notice: Subject to any disclaimer, the term of this patent is extended or adjusted under 35 U.S.C. 154(b) by 331 days.

(21) Appl. No.: 16/775,015

(22) Filed: Jan. 28, 2020

(65) Prior Publication Data

US 2021/0235132 A1    Jul. 29, 2021

(51) Int. Cl.
| | |
|---|---|
| *H04N 21/2187* | (2011.01) |
| *A61B 5/16* | (2006.01) |
| *H04N 21/236* | (2011.01) |
| *G10L 15/26* | (2006.01) |
| *G16H 50/00* | (2018.01) |

(Continued)

(52) U.S. Cl.
CPC ....... *H04N 21/2187* (2013.01); *A61B 5/0205* (2013.01); *A61B 5/165* (2013.01); *A61B 5/378* (2021.01); *A61B 5/38* (2021.01); *G06Q 30/0201* (2013.01); *G10L 15/22* (2013.01); *G10L 15/26* (2013.01); *G16H 50/00* (2018.01); *H04N 5/445* (2013.01); *H04N 7/08* (2013.01);

(Continued)

(58) Field of Classification Search
CPC ......... H04N 21/2187; H04N 21/23614; H04N 5/445; H04N 7/08; G16H 50/00; G10L 15/22; G10L 15/26; G06Q 10/101; G06Q 30/02; G06Q 30/0201; G06Q 30/0278; G06F 16/95; A61B 2503/12; A61B 5/0205; A61B 5/024; A61B 5/165; A61B 5/378; A61B 5/38
See application file for complete search history.

(56) References Cited

U.S. PATENT DOCUMENTS 10,834,298 B1 * 11/2020 Koetter ................ H04N 5/04
2014/0150002 A1 * 5/2014 Hough ............... H04N 21/4532
725/9

(Continued)

FOREIGN PATENT DOCUMENTS

WO    WO2019068025 A1    4/2019

OTHER PUBLICATIONS

PCT Search Report and Written Opinion dated Apr. 6, 2021 for PCT Application No. PCT/US21/12405, 12 pages.

*Primary Examiner* — Rong Le
(74) *Attorney, Agent, or Firm* — Lee & Hayes, P.C.

(57) ABSTRACT

A platform configured to provide virtual glass in order to augment and improve focus group sessions for each actor within the ecosystem. The platform may be configured to allow a moderator, one or more test subjects, and one or more client users to participate in a focus group session at geographically diverse locations. The platform may also be configured to supplement the focus group experience by allowing for dialog and communication between the client users. In some cases, the platform may also be configured to generate and provide real time status indicators associate with the tests subject, real time text-based transcripts of the sessions, and recommendations as to the focus group direction to the moderator.

20 Claims, 11 Drawing Sheets

(51) Int. Cl.
*A61B 5/0205* (2006.01)
*G10L 15/22* (2006.01)
*G06Q 30/02* (2012.01)
*H04N 5/445* (2011.01)
*H04N 7/08* (2006.01)
*A61B 5/024* (2006.01)
*A61B 5/38* (2021.01)
*A61B 5/378* (2021.01)

(52) U.S. Cl.
CPC ........ H04N 21/23614 (2013.01); *A61B 5/024* (2013.01); *A61B 2503/12* (2013.01)

(56) References Cited

U.S. PATENT DOCUMENTS

| | | | |
|---|---|---|---|
| 2014/0198173 A1* | 7/2014 | Willig | H04L 67/02 |
| | | | 348/14.06 |
| 2016/0165284 A1* | 6/2016 | Bargagni | H04N 21/4312 |
| | | | 725/12 |
| 2016/0210602 A1* | 7/2016 | Siddique | G06Q 20/384 |
| 2017/0011740 A1* | 1/2017 | Gauci | H04M 3/56 |
| 2018/0330736 A1* | 11/2018 | Faulkner | H04L 67/22 |
| 2019/0068996 A1* | 2/2019 | Ananthanarayanan | |
| | | | G06F 16/24545 |

* cited by examiner

SYSTEM FOR PROVIDING A VIRTUAL FOCUS GROUP FACILITY

BACKGROUND

Today, many industries, companies, and individuals rely upon physical focus group facilities including a test room and adjacent observation room to perform product and/or market testing. These facilities typically separate the two rooms by a wall having a one-way mirror to allow individuals within the observation room to watch proceedings within the test room. Unfortunately, the one-way mirror requires the individuals to remain quiet and in poorly lit conditions. Additionally, the individual observing the proceedings is required to either be physically present at the facility or rely on a written report or summary of the proceeding when making final product related decisions.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
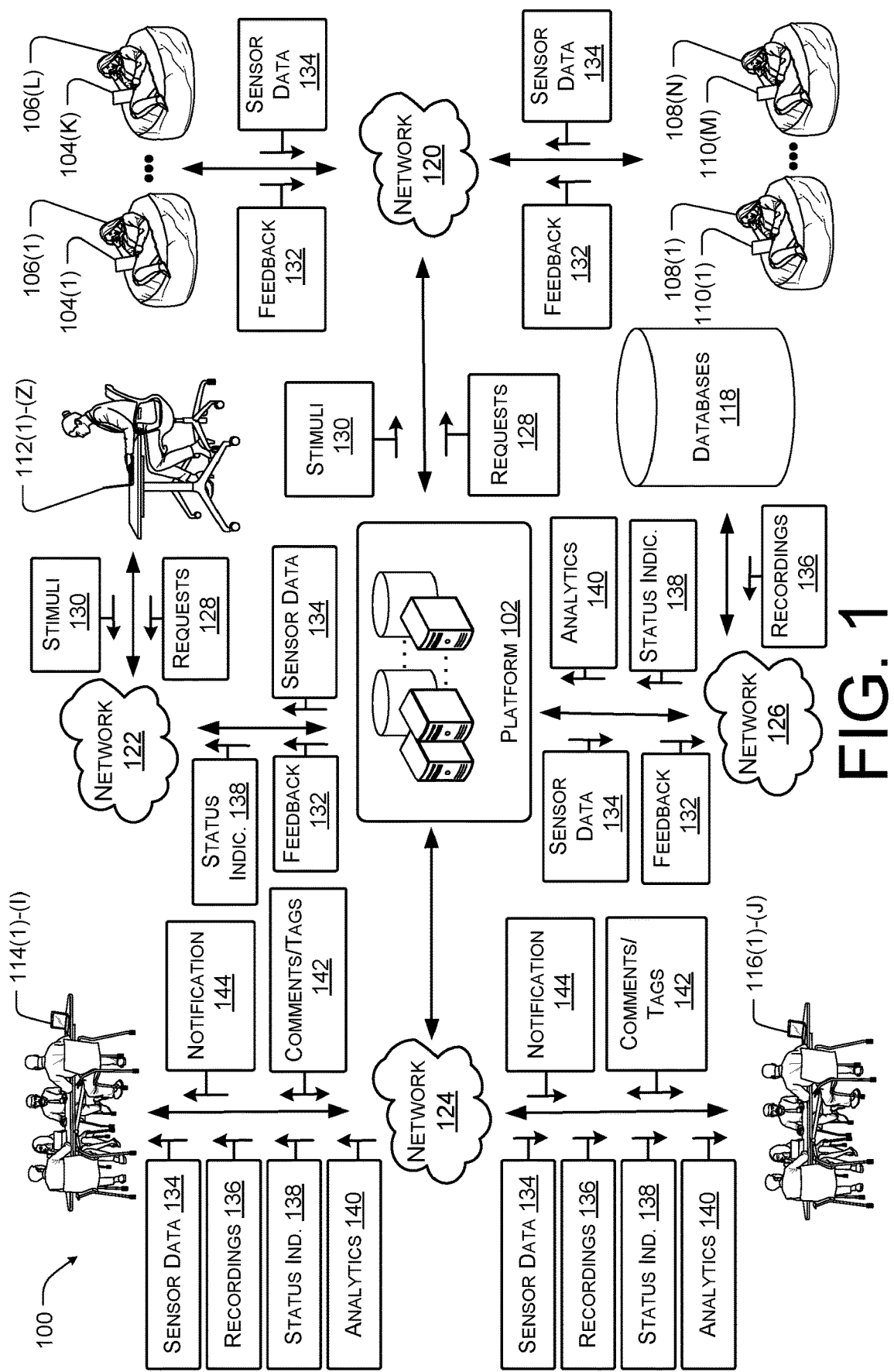
FIG. 1 illustrates an example architecture of a virtual focus group platform according to some implementations.

Described herein are devices and techniques for a virtual focus group facility via a cloud-based platform. The focus group platform, discussed herein, replicates and enhances the one-way mirror experience of being physically present within a research environment by removing the geographic limitations of the traditional focus group facilities and augmenting data collection and consumption by users via a virtual glass experience for the end client and real-time analytics. For example, the virtual glass may allow a moderator or other administer to view a focus group or other proceeding via a live stream of the audio and video data while augmenting the view experience by providing for additional data related to the focus group to be displayed or presented in conjunction with or superimposed on the audio and video stream. In some cases, the augmented data may be displayed over the live stream, such as in conjunction with the individual test subject that the data relates. In other cases, the platform may allow for a multi-device view experience in which one device displays the augmented live stream while an auxiliary or secondary device allows individual viewers of the live stream to annotate the live stream, receive and/or annotate a substantially real-time transcript of the live stream, chat or otherwise discuss the proceeding with other viewers, etc. label individual test subjects. Thus, the platform discussed herein, creates a focus group experience that enhances the experience for each of the actors, including the moderator, test subjects, and clients viewing the sessions.

In some implementations, the platform may include a test subject system or service, a moderator system or service, and a one or more component or device client system or service. Each of the systems or services may be accessible via one or more electronic devices, such that the test subjects, moderators, and/or clients may be physically remote from each other during a session. For example, the moderator may be located at their office or place of work and the test subject may be located within their home (e.g., to provide increased comfort and/or a test environment that is more representative to a real-life situation than a physical test room). The clients may also include a plurality of employees or individuals that may observe the proceedings of the session from multiple physical locations, such as is common in today's international corporate environment. For example, a first individual client may be located in New York City and a second individual client may be located in San Francisco, both of which are able to participate in the session without incurring the costs and disruption of traveling.

In some cases, the moderator may be able to communicate (e.g., text, audio, and/or video) with one or more test subjects via the platform. For example, the moderator may be able to pose questions, present stimulus (e.g., images, text, audio, or other content), or otherwise communicate with one or more test subjects. For instance, the moderator may be able to cause audio and/or visual content to display on a test subject device while asking the test subject to rate an emotional state or feeling that is invoked by the presented content in a manner similar to displaying content in a shared physical test room. In some situations, the moderator may be in communication with a single test subject to replicate a traditional physical test room situation. However, the platform may allow the moderator to communicate with multiple test subjects substantially simultaneously without each of the test subjects being aware of the others. For example, since the test subjects may be located at physically distant facilities (e.g., within their homes), the platform may allow the moderator to provide content to each subject's electronic device and to ask each subject the same or similar questions. In this manner, the platform allows for a one on one experience for the test subject but also allows the moderator to test multiple subjects substantially simultaneously, thereby, reducing the overall costs associated with conventional product and/or market testing.

The platform also improves the overall experience of the clients observing the session. For example, the platform may replicate the experience of a one-way mirror by capturing image (e.g., video) and audio data from each of the test subjects as well as the moderator (for instance, via a camera associated with the test subject device and/or moderator electronic devices) and presenting the image and audio data to each of the clients via a first device (e.g., a television). In this manner, the television may act as a virtual glass for the clients to view the session. In addition to replicating the one-way mirror of the conventional facility, by utilizing a virtual glass the clients are no longer required to sit in a poorly lighted room nor to maintain a quiet atmosphere (e.g., if two clients are co-located they may discuss the session in real time rather than simply taking notes to discuss later). Similarly, the test subject's experience is also improved as the test subjects are no longer required to sit in a mirrored room that may feel like an interrogation chamber. In some cases, the improved experience by the test subject also relates directly to improved results and better data collection. Thus, the platform, described herein, is able to improve the overall conventional focus group facility by not only reducing costs, but by improving the user experience and facility conditions.

In some implementations, in addition to collecting image and audio data from the test subjects, the platform may also be configured to capture biometric data related to the test subject, such as heartbeat/heartrate data, brain activity, temperature, type and amount of motion (e.g., is the test subject fidgeting, walking, standing, siting, etc.), focus or eye movement data, among others. The platform may be configured to analyze the captured biometric data for each test subject and to generate various status indicators that may be presented to both the moderator and/or the clients. In some cases, the types of status or amount of data presented to the moderator may differ from the status indicators or amount of data presented to the clients to assist the moderator in quickly analyzing and understanding conditions associated with the test subjects. For example, the status indicators for the moderator may include colors, ratings, or icons such as red for negative mood, green for positive mood, smiley face for happy, laughing face for amused, etc. The status indicators for the clients may be more detailed and include brain activity, blink rate, facial expression analysis, voice analytics, electroencephalography (EEG) sentiment analysis, visual fixation rate, eye position or eye movement/tracking analysis, Galvanic skin response, response latency, body posture analysis, and/or heart rate graphs to further show a subject's response to various stimulus.

In some examples, the platform may also capture and collect environmental data (e.g., room temperature, background noise, other individuals in the environment, etc.). The environmental data may be used in conjunction with the biometric data to inform the status indicators. For example, if it is too hot in a room, the platform may lower one or more thresholds associated with the biometric data such that assigning a positive attitude of the test subject may require a lower threshold than when the test subject is in a comfortable temperature zone.

In some implementations, the platform may also process the image data and/or audio data to supplement or assist with generating the status indicators. For example, the platform may detect facial expressions as the subject responds to stimulus presented on the subject device. In another example, the platform may detect focus or eye moment in relation to the content on the subject electronic device, such as to determine a portion of the content attracting the subjects focus. In some implementations, the platform may also perform speech to text conversion in substantially real time on audio data captured from the moderator and/or each test subject. In these implementations, the platform may also utilize text analysis and/or machine learned models to assist in generating the status indicators. For example, the platform may perform sentiment analysis that may include detecting use of negative words and/or positive words and together with the image processing and biometric data processing generate more informed status indicators. In some cases, the platform may aggregate or perform analysis over multiple test subjects. For instance, the platform may detect similar words, (verbs, adjectives, etc.) used to in conjunction with discussion of similar content, questions, stimuli, and/or products by different test subjects. In some cases, the platform may generate a report linking related sessions with different test subjects to reduce overall time associated with generating and reviewing test reports. In some cases, the reports are searchable such that a high-level summary may be provided by the platform that is linkable to corresponding data and/or recordings of the various associated sessions. For example, a CEO may receive the high-level summary and determine that the CEO should review all instances of negative feedback of a product generated by test subjects having a particular demographic (e.g., gender, age, social economic status, etc.) and the platform may cause portions of the associated session recordings to be sent to a device associated with the CEO.

As discussed above, the platform collects various types of data related to the test subject and/or the testing environment. The platform may then generate status indicators related to the test subject and/or the environment, aggregate subject data, derive trends, respective, or common feedback from the test subjects, and suggest questions to the moderator based on various models, thresholds, and the collected data.

The platform may also present the text in conjunction with the image and audio data on the first client device in substantially real-time. In some cases, the platform may also present the text to the individual clients via a second device. For instance, the image and audio data may be presented on a first device (e.g., a television or other electronic device with a large screen) that allows for a large viewing experience while the text (and in some instances the image data) is presented on a second device. In this manner, the first device may act as the virtual glass for the clients while the second device allows the clients to take notes, add comments, rewind, revisit, review particular portions of the session via a session recording.

In some examples, the platform may also allow multiple clients to interact with each other while viewing the recording session presented on the second client devices. For instance, the platform may allow for audio or text-based chat between the clients via the second devices as well as text-based or audio-based annotation, tagging, or notes. In other instances, the platform may provide a notification or alert to each client when other clients add comments, notes, or other annotations to the recording. In some implementations, the platform may include client identifiers and/or allow clients to annotate other client's annotations. In this manner, each client may be aware of what other clients are finding interesting within the session and further facilitate real time conversation and commentary on the session that is typically suppressed in conventional focus group facilities.

The platform may also, in some cases, allow for communication between one or more clients and the moderator. In some examples, the communication between the client and the moderator may be one way from the client to the moderator as the moderator may be in conversation with the test subject during the session. In these examples, the communication may include short text-based messages that the clients may send to the moderator to assist the moderator in understanding the direction the client would like the session to take.

FIG. 1 illustrates an example architecture 100 of a virtual focus group platform 102 according to some implementations. In the current example, the platform 102 may be in wireless communication with one or more test subject devices 104(1)-(K) associated with a first set of test subjects 106(1)-(L) as well as one or more test subject devices 108(1)-(N) associated with a second set of test subjects 110(1)-(M). The platform 102 is also in wireless communication with one or more moderator systems 112(1)-(Z). Thus, the current example, illustrates a platform 102 configured to facilitate a focus group consisting of one or more test subjects (e.g., the first set of test subjects 106 and the second set of test subjects 110) and conducted or lead by one or more remote moderators or moderator systems 112. It should be understood that the first set of test subjects 106(1)-(L) may be physically remote from the second set of test subjects 110(1)-(M) and that each test subjects 106(1)-(L) and 110(1)-(M) may receive data (e.g., requests 128 and stimuli 130) from the moderator system 112 via multiple devices, generally illustrated as the devices 104(1)-(K) and 108(1)-(N). Similarly, each test subjects 106(1)-(L) and 110(1)-(M) may be able to provide feedback 132 to the moderator system 112 via the corresponding devices 104(1)-(K) and 108(1)-(N).

In some implementations, the focus group may be conducted or lead by a moderator via the moderator systems 112. The platform 102 may be configured to allow the moderator may generate requests 128 and provide stimuli 130 to evoke a response from the test subjects 106(1)-(L) and 110(1)-(M) via the moderator system 112 and the test subject devices 104(1)-(K) and 108(1)-(N). The requests 128 may include questions provided as either text, images, video, audio, or a combination thereof. For example, the requests 128 may include an audio/video stream of the moderator that is provided to the test subjects 106(1)-(L) and 110(1)-(M) in the manner of a video chat session. In some instances, the video chat session may allow the moderator to communicate with a particular test subject 106(1)-(L) and 110(1)-(M) in a conversational two-way communication similar to being one on one in the same physical environment. However, it should be understood, that in some implementations, such as when the moderator is leading a focus group consisting of multiple test subjects 106(1)-(L) and 110(1)-(M) at different physical locations, the requests 128 may provide for one-way communication from the moderator to the test subjects 106(1)-(L) and 110(1)-(M). In the implementation in which the video/audio stream is one-way, the test subjects 106(1)-(L) and 110(1)-(M) may provide feedback 132 by entering, selecting, typing, or otherwise providing user inputs via the test subject devices 104(1)-(K) and 108(1)-(N). For instance, the requests 128 may include a polling features that may allow the moderator to question the test subjects 106(1)-(L) and 110(1)-(M). As an illustrative example, the polling question may include a request 128 to the test subjects 106 and 110 to rate an advertisement being presented to the test subjects 106(1)-(L) and 110(1)-(M). In this instance, the test subjects 106(1)-(L) and 110(1)-(M) may provide feedback 132 by typing or selecting a rating (such as selecting a number from 1-10 or turning a dial up or down).

In the instance discussed above, the test subjects 106(1)-(L) and 110(1)-(M) are responding or rating an advertisement (e.g., the stimuli 130 provided by the moderator). For example, the moderator or the moderator system 112 may be configured to cause the advertisement or other content to be displayed to the test subjects 106(1)-(L) and 110(1)-(M) via the test subject devices 104(1)-(K) and 108(1)-(N). A non-exhaustive list of the stimuli 130 may include images, video clips, audio, tactile responses, or combinations thereof that may be selected, generated, and/or provided by the moderator system 112 to the test subject devices 104(1)-(K) and 108(1)-(N) via the platform 102.

In some examples, the test subject devices 104(1)-(K) and 108(1)-(N) may also be configured to or adapted to capture various types of sensor data 134 associated with the corresponding test subjects 106(1)-(L) and 110(1)-(M) and to provide the sensor data 134 to the platform 102 and the moderator system 112. For example, the sensor data 134 may include image data (e.g., video data), audio data, biometric data (e.g., brain activity, heartrate, blink rate, EEG sentiment, visual fixation rate, Galvanic skin response, response latency, temperature, etc.), environmental data (e.g., room temperature, room occupancy, etc.). In the current example, the test subject devices 104(1)-(K) and 108(1)-(N) may be configured to capture the sensor data 134, however, it should be understood that in some implementations, distinct devices may be utilized to capture different types of sensor data 134. For instance, the test subjects 106(1)-(L) and 110(1)-(M) may be located in a room that includes separate microphones or microphone arrays, cameras, biometric data collection devices (e.g., gloves, headsets, body sensors, etc.), and/or environmental sensors (e.g., smart thermostat).

In one specific example, the moderator system 112 or the platform 102 may be configured to suggest or recommend stimuli 130 to the moderator and/or send directly to the test subject devices 104(1)-(K) and 108(1)-(N) (such as in a platform 102 that implements as autonomous or virtual moderator). For instance, using the feedback 132 and/or the sensor data 134 as an input, the moderator system 112 or the platform 102 may select or determine the next stimuli 130 and/or request 128 based on the output of one or more heads of a machine learned model or neural network.

In some implementations, the platform 102 and/or a remote database 118 may be configured to receive the sensor data 134 and/or the feedback 132 and to generate a recording 136 of the session. In some cases, the platform 102 and/or the remote database 118 may generate the speech-to-text version or transcript of the captured audio from either or both of the moderator and the test subjects 106(1)-(L) and 110(1)-(M). In some examples, the transcript may be translated into one or more secondary languages and presented to the client systems 114 and 116 based on a preferred language of the corresponding client or clients. The recording 136 may then include both the audio/video data as well as linked or otherwise associated text version of the audio data. In this way, the recording 136 may be viewed in segments based on one or more searches (e.g., as a text-based search) to reduce the overall time to review each session. In one specific example, the recording 136 may be generated in substantially real-time, such that an individual watching the session may also receive the text-based version without significant gaps in time.

The platform 102 and/or the remote database 118 may also generate various types of status indicators 138 and/or analytics 140 associated with one or more sessions or individual test subjects 106 or 110 of the session. For example, the platform 102 and/or the remote database 118 may detect facial expressions from the image data of the sensor data 134 as the subject responds to the stimulus 130 presented on the subject device. In another example, the platform 102 and/or the remote database 118 may detect focus or eye moment in relation to the content on the subject device, such as to determine a portion of the stimulus 130 (e.g., content) attracting the subject's focus. In still other examples, the platform 102 and/or the remote database 118 may process the biometric data to determine a mood (e.g., happy if a test subjects 106 or 110 heartrate increases above a threshold). In some examples, the status indicators 138 may be a color such as green for happy, yellow for calm, red for anger, etc. or an icon such as a laughing face for amused, a crying face for sad, etc. to allow the moderator to quickly determine the mood of the test subjects 106 or 108. In some examples, common status indicators 138 may be shown to, for instance, the moderator via the moderator system 112 or the clients via the client systems 114 and 116 as a text bubble, circle, or icon that has the designated colors or numerical values (such as 1-10) as part of the augmented virtual glass experience and/or superimposed on the image of the corresponding test subject. In some examples, less common status indicators 138 may be provided as textual data, such as an indicator related to the tests subject falling asleep during the session. In some examples, in addition to the status indictors 128, various demographic data may be displayed as par to of virtual glass experience and/or superimposed on the image of the corresponding test subject to the moderator and/or the clients. For instance, images of each of the test's subjects (either live feeds or still images) may be displayed on the moderator device together with the augmented data (e.g., the status indicators 138). In this instance, below the image of each test subject may include various data related to the test subject such as name, age, sex, race, socially economic status, etc. Thus in the platform 102, the moderator no longer has to rely on notes or memory when conducting the session as the information may be presented on the moderator system 112 in an easily consumable manner and updated in substantially real-time.

In the case of multiple test subjects 106(1)-(L) and 110(1)-(M), the platform 102 may attach or insert the status indicators 138 over or adjacent to the image of the corresponding test subjects 106(1)-(L) and 110(1)-(M) to further assist the moderator in determining which individual test subjects 106(1)-(L) and 110(1)-(M) is experiencing which emotion. Additionally, in some instances, the status indicator 138 may also include an aggregated indicator showing an overall mood or status of the group of test subjects 106(1)-(L) and 110(1)-(M). For example, the aggregated indicators may be based on normalized biometric or emotional data collected from a large sample (for instance, greater than or equal to 70 test subjects or greater than or equal to 140 test subjects) and then the sensor data 134 associated with the current test subjects 106 and 110 may be compared to the normalized data to provide a score or more meaningful metric or status indicator 138. In some cases, the benchmarked data may be specific to demographics associated with the test subjects, similar session topics (e.g., consumer products versus political topics), among others.

The platform 102 and/or the remote database 118 may also aggregate or otherwise determine trends or analytics 140 based on the sensor data 134 collected from one or more sessions. For example, the platform 102 may perform audio, video, or text analysis on the recording 136 to identify common trends (e.g., similar responses from different test subjects 106 or 110), similar emotional responses, unique responses, etc. and to present, such as in a chart or graph, for instance, as part of the recording 136. In some specific examples, the platform 102 and/or the remote database 118 may also identify questions or stimuli to recommend to the moderator based on the analytics 140 and/or the status indicators 138.

In some implementations, the platform 102 and/or the remote database 118 may process the sensor data 134 via one or more machine learned models or neural networks to generate the status indicators 138 or generate the analytics 140. For example, machine learning techniques may include, but are not limited to, regression algorithms (e.g., ordinary least squares regression (OLSR), linear regression, logistic regression, stepwise regression, multivariate adaptive regression splines (MARS), locally estimated scatterplot smoothing (LOESS)), instance-based algorithms (e.g., ridge regression, least absolute shrinkage and selection operator (LASSO), elastic net, least-angle regression (LARS)), decisions tree algorithms (e.g., classification and regression tree (CART), iterative dichotomiser 3 (ID3), Chi-squared automatic interaction detection (CHAID), decision stump, conditional decision trees), Bayesian algorithms (e.g., naive Bayes, Gaussian naive Bayes, multinomial naive Bayes, average one-dependence estimators (AODE), Bayesian belief network (BNN), Bayesian networks), clustering algorithms (e.g., k-means, k-medians, expectation maximization (EM), hierarchical clustering), association rule learning algorithms (e.g., perceptron, back-propagation, hopfield network, Radial Basis Function Network (RBFN)), deep learning algorithms (e.g., Deep Boltzmann Machine (DBM), Deep Belief Networks (DBN), Convolutional Neural Network (CNN), Stacked Auto-Encoders), Dimensionality Reduction Algorithms (e.g., Principal Component Analysis (PCA), Principal Component Regression (PCR), Partial Least Squares Regression (PLSR), Sammon Mapping, Multidimensional Scaling (MDS), Projection Pursuit, Linear Discriminant Analysis (LDA), Mixture Discriminant Analysis (MDA), Quadratic Discriminant Analysis (QDA), Flexible Discriminant Analysis (FDA)), Ensemble Algorithms (e.g., Boosting, Bootstrapped Aggregation (Bagging), AdaBoost, Stacked Generalization (blending), Gradient Boosting Machines (GBM), Gradient Boosted Regression Trees (GBRT), Random Forest), SVM (support vector machine), supervised learning, unsupervised learning, semi-supervised learning, etc. Additional examples of architectures include neural networks such as ResNet50, ResNet101, VGG, DenseNet, PointNet, and the like.

In the illustrated example, the platform 102 may also be in wireless communication with a first set of client systems 114(1)-(I) and a second set of client systems 116(1)-(J). It should be understood that the first set of client systems 114 may be physically remote from the second set of client systems 116 and that each system 114 and 116 may include multiple devices to present data and/or receive user inputs from one or more clients. For example, a first client may receive the audio/video stream to a first device (e.g., a television) and the recording 136 (e.g., the audio, video, and text-based data associated with the session) via a second device (e.g., a tablet or computer). Thus, the television may act as the virtual glass to allow the clients to view the session in a manner similar to being present in an observation room and the tablet or computer may allow the client to take notes add comments or tags 142 to the recording 136 which may be reviewed at a later time. In some examples, the recording 136 may also include the status indicators 138 and the analytics 140 as an integrated features or component.

In some implementations, the clients may be able to annotate (e.g., comment or tag 142) content within the recording 136. In some cases, the comments and/or tags 142 may be added to a global recording 136 and become visible to the other client systems 114(1)-(I) and 116(1)-(J) to facilitate conversation. In addition to adding each client's comments and tags 142 to the global recording 136, the platform 102 may also generate an alert or notification 144 to the other client systems 114(1)-(I) and 116(1)-(J) in response to an individual client adding a comment or tag 142. In some cases, the notification 144 may be visual queues (e.g., icon, flashing, color change, etc.) or audio queues (e.g., output a sound). In some instances, the notifications 144 may be associated with a specific client. For example, if a first client adds a comment or tag 142, the platform 102 may cause a first notification (e.g., a red flashing icon) to be output by the client systems 114(1)-(I) and 116(1)-(J) and, if a second client adds a comment or tag 142, the platform 102 may cause a second notification (e.g., a green flashing icon) to be output by the client systems 114(1)-(I) and 116(1)-(J). in this manner, each client may quickly determine if they desire to review the comment or tag 142 being added based on the individual adding the comment or tag 142. In some implementations, the analytics 140 may be updated based on the comments or tags 142 being added by the clients. For instance, the platform 102 may identify the most or least commented section of a session or each portion (e.g., 5-15 second portion) of a session that received more than a threshold number of comments or tags 142. In some implementations, visibility of the comments and tags 142 may be controlled by the client that is adding the comment or tag 142. For instance, the comments and tags 142 may be personal, shared with a group, or shared globally.

Figure 2:
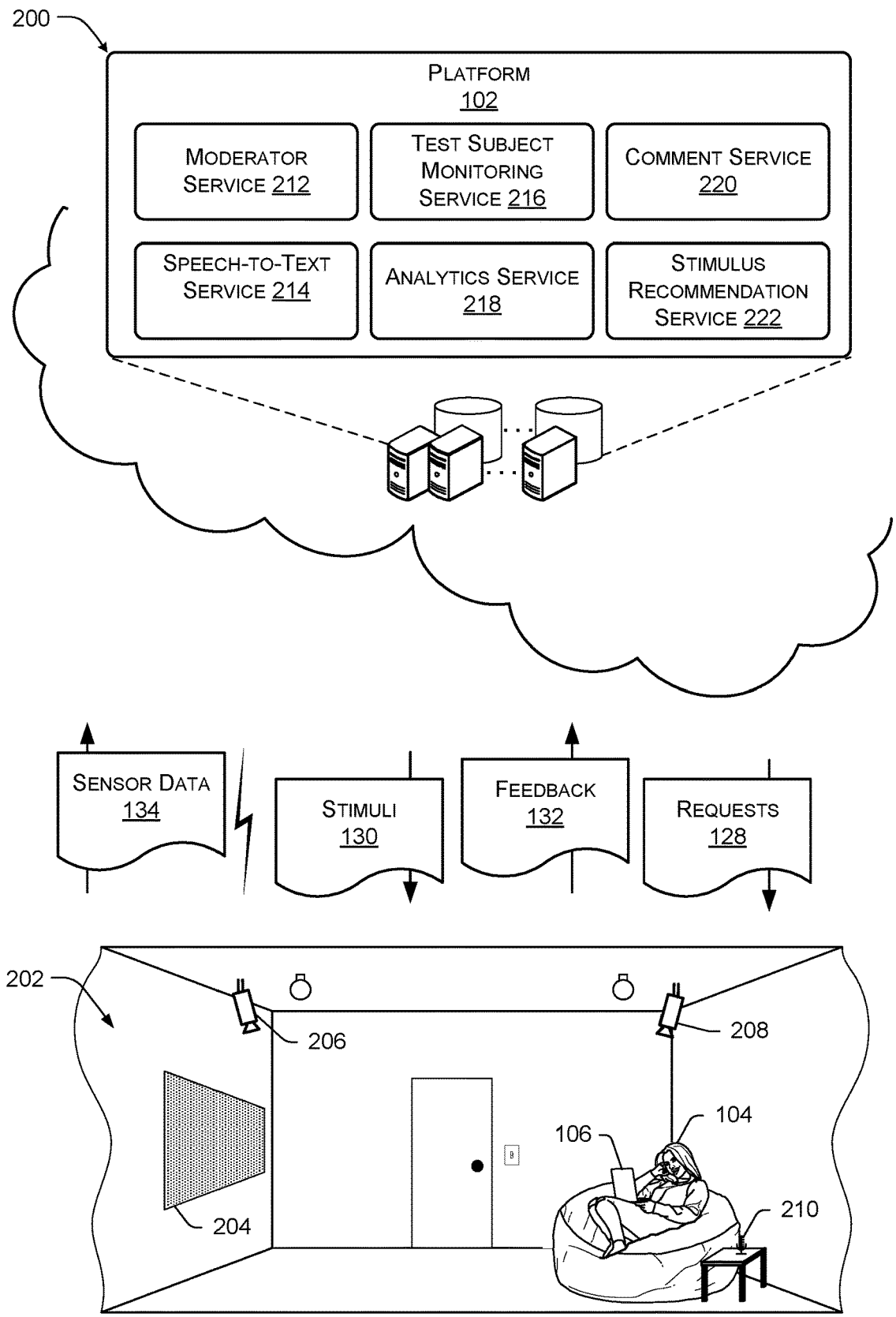
FIG. 2 illustrates an example pictorial view of a test subject participating in a session facilitated by a virtual focus group platform according to some implementations.

FIG. 2 illustrates an example pictorial view 200 of a test subject 104 participating in a session facilitated by a virtual focus group platform 102 according to some implementations. In the illustrated example, the test subject 104 is located within a room 202, such as the test subject's living room. Thus, unlike conventional focus group facilities, the test subject 104 may perform the session in the comfort of their own home.

The test subject 104 is conducting a focus group session with a moderator (not shown) via an application installed on the test subject device 106. For instance, the platform 102 may send stimuli 130 and/or requests 128 to the test subject 104 via the test subject deice 106. Similarly, the platform 102 may receive feedback 132 from the test subject via the client device 106. In this example, the test subject 104 may also view content or stimuli 130 presented via the television or display 204. Thus, it should be understood, that the platform 102 is configured to allow for a multi-device interaction for the test subject 104 to more closely recreate the physical focus room experience. For instance, the user may view an advertisement on the display 204 while answering questions on the device 106. In this manner, the test subject 104 may consume or review content or stimuli 130 via the test subject device 106 and/or the display 204.

In the illustrated example, the room 202 also includes various sensors, such as cameras 206 and 208 and microphone array 210. In some cases, the test subject 104 may also wear various biometric data collections devices (not shown), such as heartrate monitors or brain activity monitors. In general, the data collection devices 206-210 may capture data related to the session from the environment or room 202 and send to the platform 102 as sensor data 134, as discussed above with respect to FIG. 1.

In the current example, the platform 102 may include various cloud-based or remote services associated with conducting virtual focus groups. For example, the platform 102 may include a moderator service 212, a speech-to-text service 214, a test subject monitoring service 216, an analytics service 218, a comment service 220, and a stimulus recommendation service 222.

The moderator service 212 may be configured to allow a moderator to communicate and/or provide stimuli 130 and requests 128 to the test subject via the display 204 and/or the device 106. In some implementations, the moderator service 212 may be configured to conduct the session with the test subject as an autonomous system. For instance, the moderator service 212 may be configured to conduct preprogramed sessions (e.g., a series of stimuli 130 and requests 128). In other instances, the moderator service 212 may be configured to utilize one or more machine learned model, neural network, and/or output of the other services 214-222 to analyze the sensor data 134 and to select requests 128 and stimuli 130 to provide to the test subject 104.

The speech-to-text service 214 may be configured to receive the audio portion of the sensor data 134 and to convert the audio data into a text-based transcript. In some cases, the speech-to-text service 214 may correlate or relate the text-based transcript with the audio and/or video data to generate a recording in substantially real-time, as discussed above with respect to FIG. 1.

The test subject monitoring service 216 may be configured to analyze the sensor data 134 collected from the environment or room 202 and to generate the status indicators associated with the test subject. As discussed above, the test subject monitoring service 216 may utilize various machine learned models, numeral networks, or other data analytic techniques when determining the status indicators. Additionally, the status indicators may be presented to clients observing the session in various formats, such as visual (e.g., icons, colors, ratings, percentages, graphs, etc.), audio (e.g., output sounds in response to changes in mood), or text-based annotations to the recordings.

The analytics service 218 may be configured to analyze the sensor data 134 collected from the environment or room 202 with respect to other sessions or other test subjects and to generate trends, common occurrences, maximum or minimum thresholds, etc.

The comment service 220 may be configured to allow clients to provide comments or tags 142 associated with the session. For example, the comment service 220 may allow the clients to add audio, video, or text-based information to the session recording. As discussed above, the comments and tags 142 may be private, shared with a select group, or global.

The stimulus recommendation service 222 may configured to assist the moderator and/or the moderator service 212 with conducting the session. For example, the stimulus recommendation service 222 may analyze the sensor data 134 collected from the environment or room 202 and to generate recommendations, sample questions, select stimulus or other content, that may be used to direct the session one way or another. For example, if the client specifies specific goals for the session, the recommendations, sample questions, stimulus or other content may be selected to assist in achieving the client goals.

Figure 3:
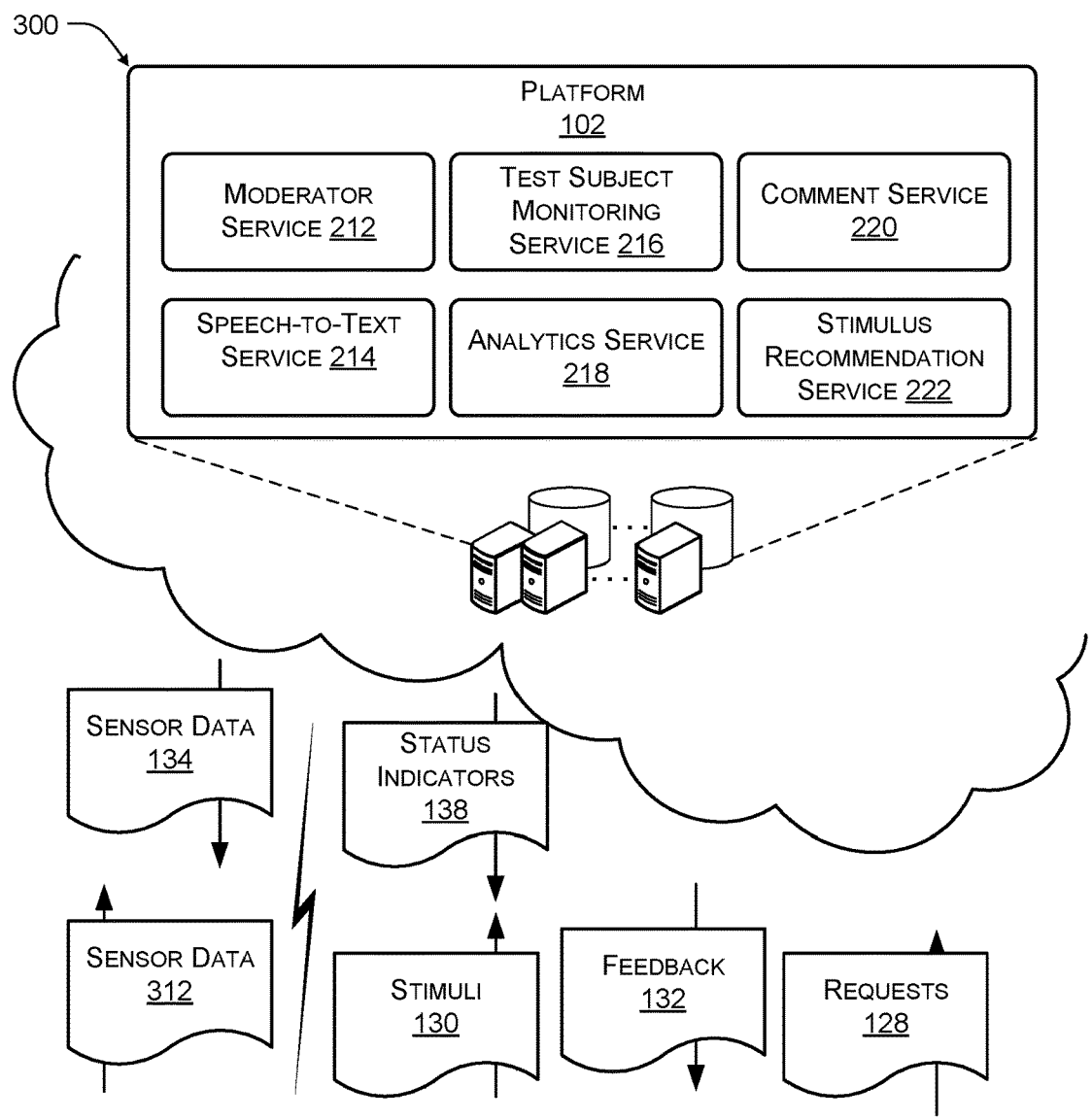
FIG. 3 illustrates an example pictorial view of a moderator participating in a session facilitated by a virtual focus group platform according to some implementations.
Figure 3:
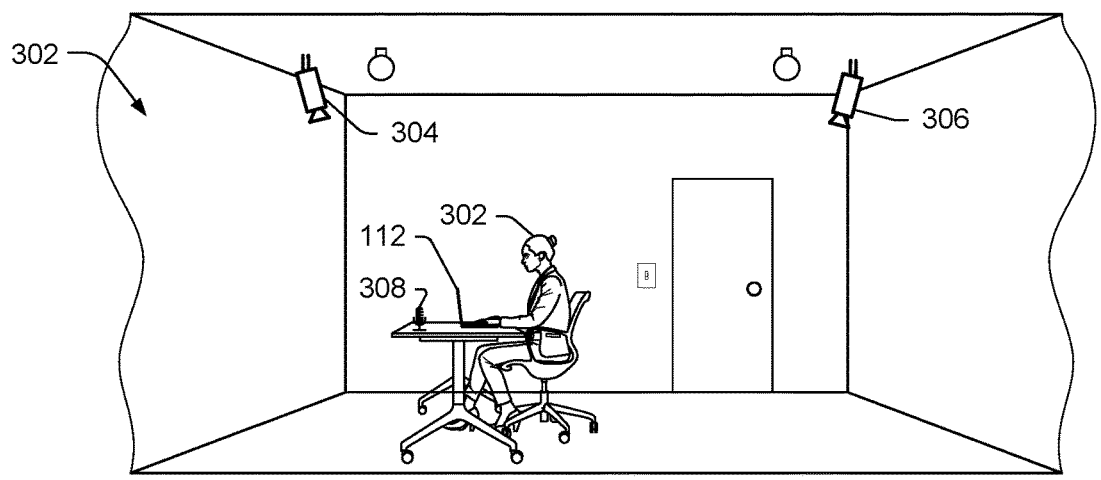

FIG. 3 illustrates an example pictorial view 300 of a moderator 302 participating in a session facilitated by a virtual focus group platform 102 according to some implementations. In the illustrated example, the moderator 302 is located within an environment 302 (moderator and environment are both 302), such as the moderator's office. The moderator 302 may conduct or lead a focus group session with one or more test subjects (not shown) via an application installed on the test subject device 112. For instance, the moderator 302 may receive an audio/video data (e.g., sensor data 134) of the test subject as well as feedback 132 via the platform 102. The platform 102 may also communicatively couple the moderator 302 with the test subject via a video chat session. The moderator 302 may also be able to provide requests 128 and/or cause stimuli 130 to be presented to the test subject via the device 112 and/or the platform 102. Thus, the moderator 302 may be in communication with the test subject as if the moderator 302 was present in the same physical location as the test subject.

In one implementation, the moderator application installed on the moderator system 112 may be configured to present session data in an organized manner to improve session flow and/or reduce complexity and distractions experienced by the moderator 302. For instance, the moderator system 112 may present an icon, video live stream, and/or image of each tests subject associated with a current session. Each icon associated with a test subject may also include one or more status indictor superimposed or associated with the icon representing the test subject. The status indicators may change in response to the platform 102 determining a change in status of the corresponding test subject based on the analytics of the captured biometric, audio, and visual data of the corresponding test subject. Additionally, the information presented to the moderator may include demographic information, polling answers, private chat messages, unique or flagged emotional responses to content, etc. In some cases, the additional data may be displayed below or adjacent to each test subject's icon.

In some cases, the moderator system 112 may allow the moderator 302 to preload or plan a session. For example, the moderator system 112 may allow the moderator 302 to preload or otherwise organize a plurality of stimuli 130, such as a series of video content that may be provided to the test subject devices during a session. In this manner, the moderator 302 does not need to interrupt the flow of a session to play a DVD via a DVD player as in a conventional focus group session. In one specific example, the platform 102 may reorganize the order or arrangement of the stored stimuli 130 based on a progression of the session as compared to prior sessions conducted by the moderator 302.

In the illustrated example, the environment 302 also includes various sensors, such as cameras 304 and 306 and microphone array 308. In general, the data collection devices 304-308 may capture data related to the session from the environment 302 and send to the platform 102 as sensor data 312 to be incorporated into the session record that is sent to the client systems.

As discussed above with respect to FIG. 2, the platform 102 may include various cloud-based or remote services associated with conducting virtual focus groups. For example, the platform 102 may include the moderator service 212, the speech-to-text service 214, the test subject monitoring service 216, the analytics service 218, the comment service 220, and the stimulus recommendation service 222.

Figure 4:
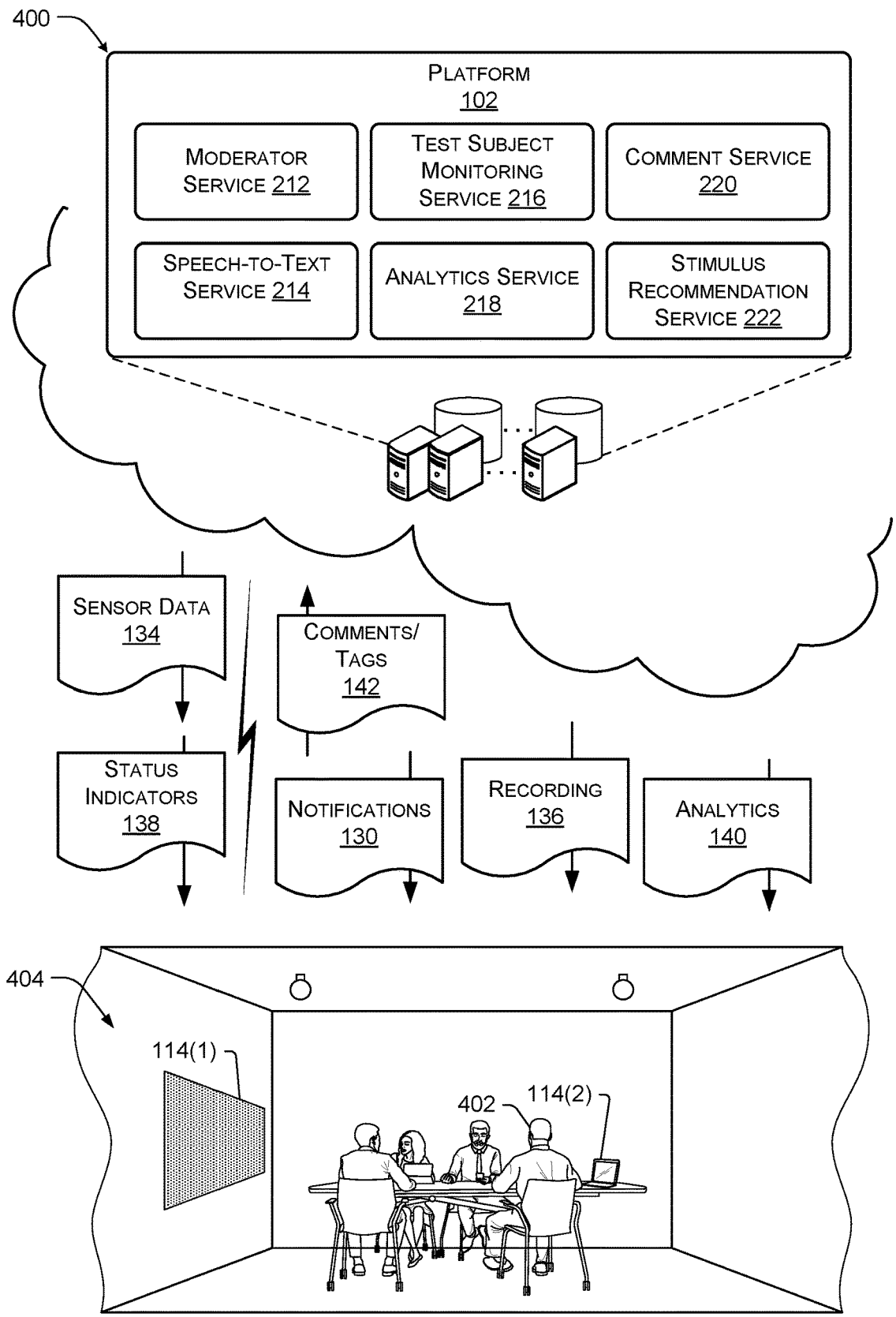
FIG. 4 illustrates an example pictorial view of a client group observing in a session facilitated by a virtual focus group platform according to some implementations.

FIG. 4 illustrates an example pictorial view 400 of a client group, generally indicated by clients 402(1)-(M), observing a session facilitated by a virtual focus group platform according to some implementations. In the illustrated example, the clients 402 are located within an environment 404, such as a conference room. The clients 402 may observe the session between the moderator and the test subjects via one or more client systems 114 (e.g., the television 114(1) and personal computing device 114(2)).

For instance, the clients 402 may watch a live stream of the session on the television 114(1). The clients 402 may also watch the session on the computing device 114(2).

In some examples, the live stream of the session on the television 114(1) may act as the virtual glass providing the augmented viewing experience. For example, the platform 102 or an administrator may configure the virtual glass display on the television 114(1) by assigned bubbles or content circles associated with or over each test subject. In some cases, the bubbles may include the test subject's demographic information, status indicators 138, as well as other analytics.

On the device 114(2), the individual clients 402 may be able to review the recording 136 (including the text-based transcript) as well as to add comments and/or tags 142 to the record 136. As discussed above, the clients may also receive notifications 144 related to the comments and tags 142 being added to the record 136 in substantially real-time. For instance, the virtual glass display on the television 114(1) may also include any comments or tags 142 provided by one or more clients 402 via the second client devices 114(2) as well as output stimuli being viewed by the test subjects. In some implementations, various sounds or other notification (e.g., flashing color, assigned colors, graphics, etc.) may display when a corresponding client 402 adds a tag or comment 142 via the second device 114(2).

In some examples, the device 114(2) may operate both as the virtual glass display mode and an interactive mode as discussed above. For example, the device 114(2) may operate in the interactive mode when in a first orientation, e.g., the client 402 may add comments and tags 142, review the recording 136 including the transcript in one or more languages, view the analytics, stop pause or rewind the recording 136, chat with other clients, etc. The device 114(2) may then operate in the virtual glass display mode when the device 114(2) is in a second orientation. For example, in the virtual glass display mode the device 114(2) may display the augmented live stream of the session similar to the television 114(1). In the virtual glass display mode, the live session may be displayed including the overlays and/or augmented data provided by the platform 102, such as the status indicators 138, demographic information, stimuli being viewed by the test subjects, alerts and notifications to other client's tags or comments, etc. Thus, in this example, the client 402 may utilize the same device 114(2) as both the virtual glass and in the interactive mode.

As discussed above with respect to FIG. 2, the platform 102 may include various cloud-based or remote services associated with conducting virtual focus groups. For example, the platform 102 may include the moderator service 212, the speech-to-text service 214, the test subject monitoring service 216, the analytics service 218, the comment service 220, and the stimulus recommendation service 222.

Figure 5:
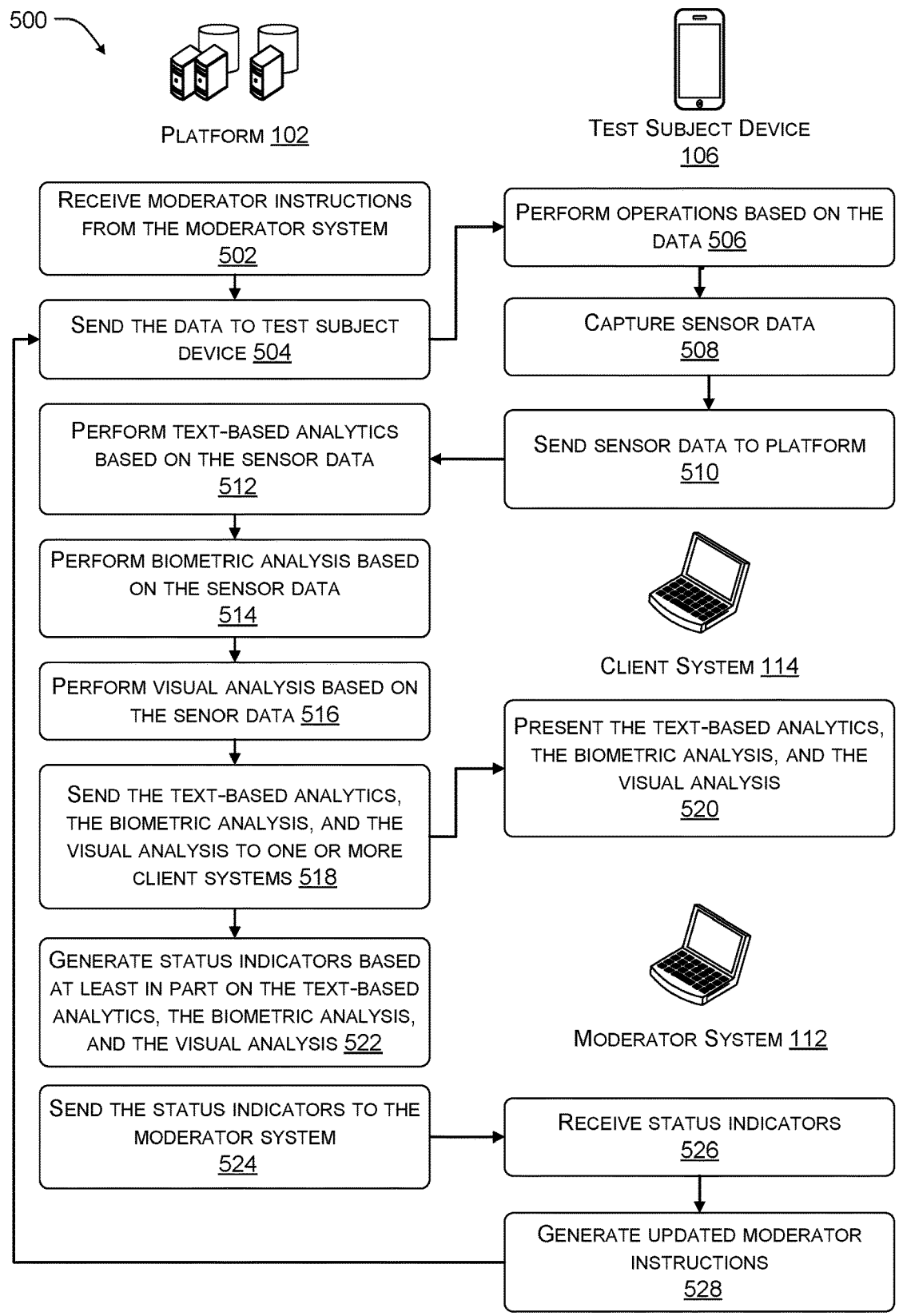
FIG. 5 illustrates an example flow diagram showing an illustrative process for providing a virtual focus group according to some implementations.
Figure 6:
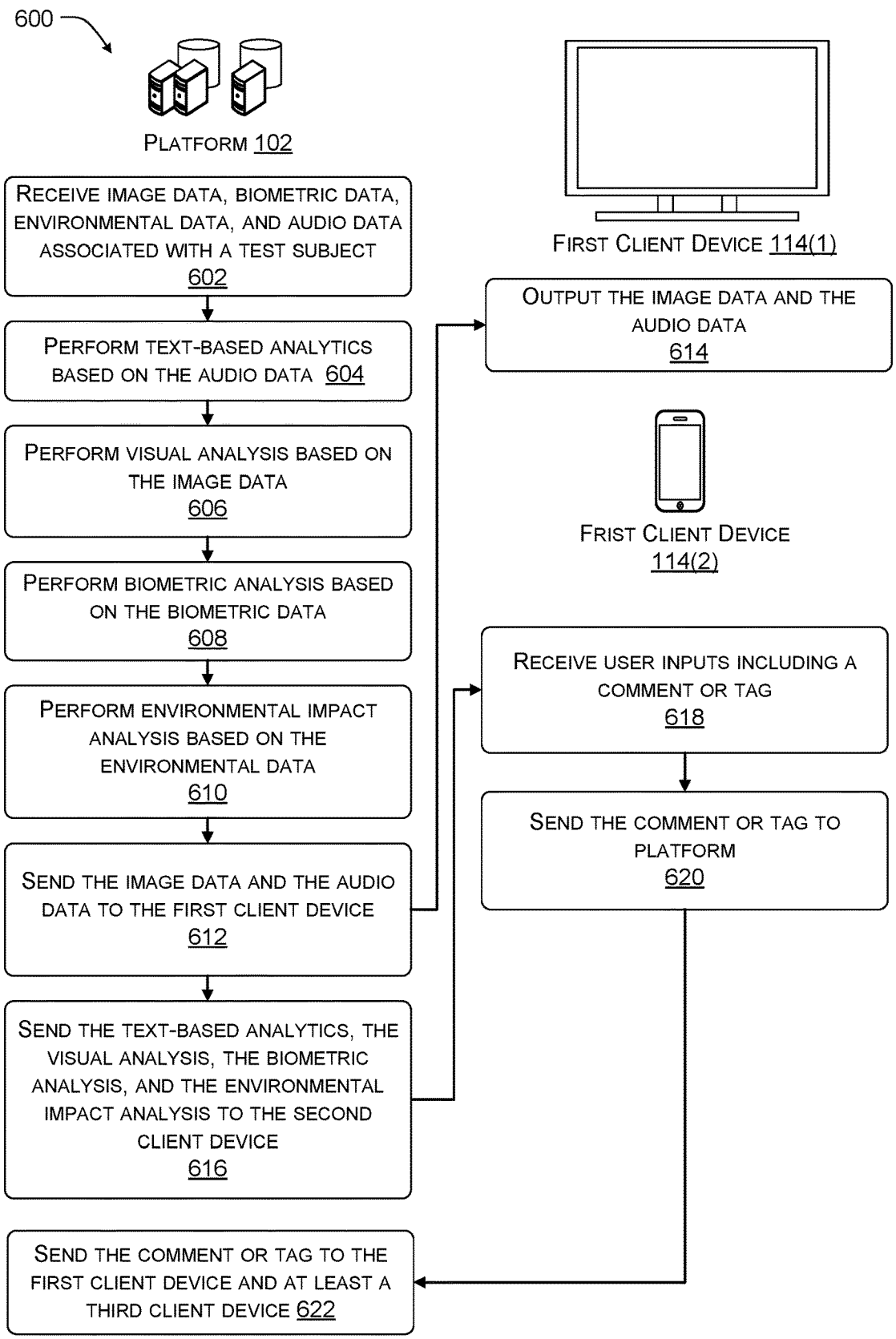
FIG. 6 illustrates an example flow diagram showing an illustrative process for providing a virtual focus group according to some implementations.
Figure 7:
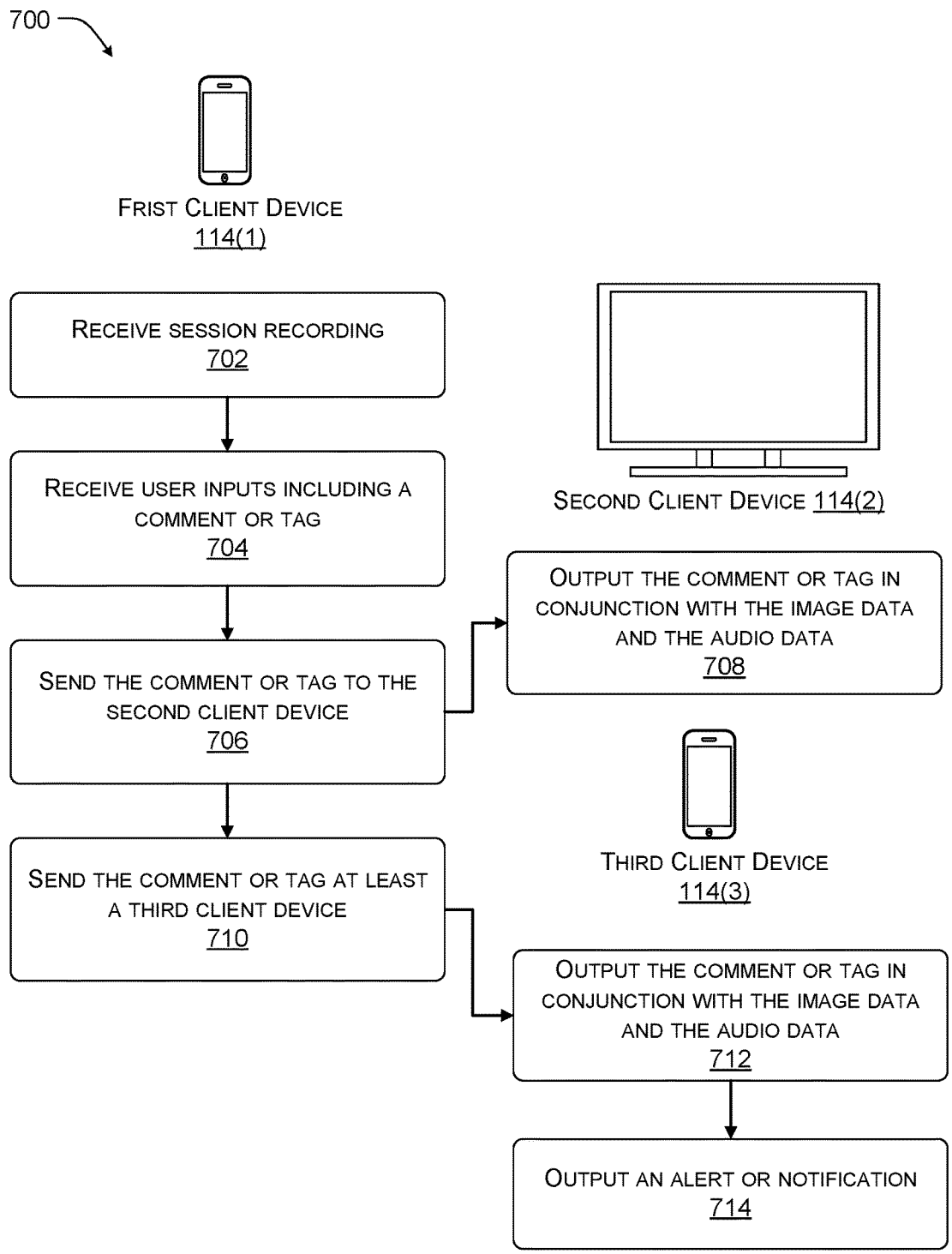
FIG. 7 illustrates an example flow diagram showing an illustrative process for providing a virtual focus group according to some implementations.

FIGS. 5-7 are flow diagrams illustrating example processes associated with the platform 102 of FIGS. 1-4 according to some implementations. The processes are illustrated as a collection of blocks in a logical flow diagram, which represent a sequence of operations, some or all of which can be implemented in hardware, software, or a combination thereof. In the context of software, the blocks represent computer-executable instructions stored on one or more computer-readable media that, which when executed by one or more processors, perform the recited operations. Generally, computer-executable instructions include routines, programs, objects, components, encryption, deciphering, compressing, recording, data structures and the like that perform particular functions or implement particular abstract data types.

The order in which the operations are described should not be construed as a limitation. Any number of the described blocks can be combined in any order and/or in parallel to implement the process, or alternative processes, and not all of the blocks need be executed. For discussion purposes, the processes herein are described with reference to the frameworks, architectures and environments described in the examples herein, although the processes may be implemented in a wide variety of other frameworks, architectures or environments.

FIG. 5 illustrates an example flow diagram showing an illustrative process 500 for providing a virtual focus group according to some implementations. As discussed above, the focus group platform, discussed herein, replicates and enhances the one-way mirror experience of being physically present within a research facility without the geographic limitations of traditional focus group facilities. In some implementations, a platform 102 may include a test subject device 106, a moderator system or device 112, and a client system or device 114.

At 502, the platform 102 may receive moderator instructions from the moderator system 112 related to a focus group session. For example, the moderator may provide instructions to present content or stimulus on a display or ask the test subject to answer one or more questions.

At 504, the platform 102 may send data to the test subject device. For example, the platform 102 may identify content, stimulus, or requests to present to the test subject based on the moderator instructions. The platform 102 may select one or more devices associated with the test subject to receive the content, stimulus, or request. In one example, the content or stimulus may be provided to a display device while the request may be provided to an input/output device.

At 506, the test subject device 106 may perform operations based on the data received. For example, the device 106 may display content or stimulus and/or request user input to requests.

At 508, the test subject device 106 (and/or other sensors associated with the test subject device 106) may capture sensor data from the environment and, at 510, the test subject device 106 sends the sensor data to the platform 102. For example, the sensor data may include image data, video data, audio data, biometric data, environmental data, among other type of data associated with the test subject.

At 512, the platform 102 may perform text-based analytics based on the sensor data. For example, the platform 102 may covert audio data captured by the test subject device 102 to text using one or more speech-to-text conversion techniques. The platform 102 may then preform text-based analytics on the text-based transcript of the audio data. For instance, the platform 102 may detect words or phrases repeated by the test subject, uncommon or unique words or phrases, words or phrases common to other test subjects, emotional words or phrases, among others.

At 514, the platform 102 may perform biometric analytics based on the sensor data. For example, the test subject device 106 may capture brain activity data, heartrate data, temperature data, or other data associated with the test subjects physical state. The platform 102 may then determine mood and/or emotional responses based at least in part on the biometric data.

At 516, the platform 102 may perform visual analytics based on the sensor data. For example, the test subject device 106 may capture image data and perform facial analysis or eye tracking on the image data. The platform 102 may then determine a mood or emotional reaction to specific content, stimuli, or requests.

At 518, the platform may send the text-based analytics, the biometric analysis, and the visual analysis to one or more client systems 114 and, at 520, the client systems 114 may present the text-based analytics, the biometric analysis, and the visual analysis to one or more client systems on a display. For example, the text-based analytics, the biometric analysis, and the visual analysis may be presented on the display in conjunction with an audio/video feed of the session.

At 522, the platform 102 may generate a status indicator based at least in part on the text-based analytics, the biometric analysis, and the visual analysis. For example, the platform 102 may determine a mood or emotional state of the test subject based at least in part on the text-based analytics, the biometric analysis, and the visual analysis which may be used to generate the status indicator, as discussed above. In other alternative examples, the platform 102 may also determine the status indictors directly from the sensor data and/or a combination of the text-based analytics, the biometric analysis, and the visual analysis, and the sensor data.

At 524, the platform 102 may send the status indicator to the moderator system 112 and, at 526, the moderator system 112 may receive the status indictors. In some cases, the moderator system 112 may present the status indicators to the moderator to assist the moderator in evaluating the status or state of the session and/or the test subject. In some implementations, the platform 102 may also send the status indicator to the client system 114. In these implementations, the status indicators sent to the moderator system 112 may be the same as or may differ from the status indicators sent to the client system 114. For example, the status indictors sent to the client system 114 may be more detailed or contain more information than the status indictors sent to the moderator system 112.

At 528, the moderator system 112 may generate updated moderator instructions, for instance, based at least in part on the status indictors and send the updated moderator instructions to the platform 102, as discussed above.

FIG. 6 illustrates an example flow diagram showing an illustrative process 600 for providing a virtual focus group according to some implementations. In some implementations, the platform 102 may be configured to replicate and enhance the conventional focus group experience. In these implementations, the experience for the client or focus group observer may be configured for multiple device, such as first client device 114(1) and second client device 114(2), interaction, as described below.

At 602, the platform 102 may receive image data, biometric data, environmental data, audio data, and/or other sensor data associated with a test subject. For example, the image data, biometric data, environmental data, audio data, and/or other sensor data may be collected or captured by a test subject device or one or more peripherals associated with the test subject device.

At 604, the platform 102 may perform text-based analytics based on the audio data collected by the test subject device. For example, the platform 102 may covert audio data captured by the test subject device 102 to text using one or more speech-to-text conversion techniques. The platform 102 may then preform text-based analytics on the text-based transcript of the audio data. For instance, the platform 102 may detect words or phrases repeated by the test subject, uncommon or unique words or phrases, words or phrases common to other test subjects, emotional words or phrases, among others.

At 606, the platform 102 may perform visual analytics based on the image data collected by the test subject device. For example, the test subject device 106 may capture image data and perform facial analysis or eye tracking on the image data. The platform 102 may then determine a mood or emotional reaction to specific content, stimuli, or requests.

At 608, the platform 102 may perform biometric analytics based on the biometric data collected by the test subject device. For example, the test subject device may capture 106 brain activity data, heartrate data, temperature data, or other data associated with the test subjects physical state. The platform 102 may then determine mood and/or emotional responses based at least in part on the biometric data.

At 610, the platform 102 may perform environmental impact analysis based on the environmental data collected by the test subject device. For example, the platform 102 may determine if it is too hot or too cold within the environment occupied by the test subject. In some cases, the platform 102 may adjust one or more of the text-based analytics, the biometric analysis, and the visual analysis based on the environmental analysis. For instance, a threshold associated with a positive test subject response may be decreased if the environmental conditions are poor and likely to aggravate the test subject.

At 612, the platform 102 may send the image data and the audio data to the first client device 114(1) and, at 614, the first client device 114(1) may output the image data and the audio data via a display. For instance, as discussed above, the first client device 114(1) may be a large display that acts as a virtual glass for viewing the test subject and/or the moderator during the session. Thus, in this example, the live audio/video stream may be presented to the display to replicate the experience of watching the session in person.

At 616, the platform 102 may send the text-based analytics, the visual analysis, the biometric analysis, and the environmental impact analysis to the second client device 114(2), such that each individual client may review the analytics and analysis at their own pace and without interrupting the virtual glass on the first client device 114(1). In some examples, the analytics and analysis may be provided to the second client device 114(2) as part of a recording of the session together with the image data and the video data.

At 618, the first client device 114(2) may receive user inputs including a comment or tag. For example, the comment or tag may be associated with a particular portion of the recording.

At 620, the first client device 114(2) may send the comment or tag to the platform 102 and, at 622, the platform 102 may send or cause the comment or tag to be displayed by the first client device 114(1) (such as, a notification as to the comment) and at least a third client device. For example, the comment or tag may be shared via a global recording or with a specific group or subset of clients.

FIG. 7 illustrates an example flow diagram showing an illustrative process 700 for providing a virtual focus group according to some implementations. As discussed above, the platform may enhance the conventional focus group experience by allowing the clients to discuss, talk, or interact with each other during the session. Conventionally, the clients located in the observation room had to maintain a state of quiet to avoid interrupting the session happening in close proximity. However, unlike the conventional facility, the platform, discussed herein, not only allows interaction but encourages it.

At 702, the first client device 114(1) associated with a first client may receive the session recording. In some cases, the session recording may be provided in substantially real-time and may include various analytics, status indictors, the audio/video data, as well as a text-based transcript of the session.

At 704, the first client device 114(1) may receive user inputs including a comment or tag. For example, the comment or tag may be associated with a particular portion of the recording. The comment or tag may include thoughts, insights, and/or questions related to the portion or the recording.

At 706, the first client device 114(1) may send the comment or tag to a second client device 114(2) and, at 708, the second client device 114(2) may output the comment or tag in conjunction with the image data and the audio data of the session. For example, the comment or tag may be shared via a global recording or with a specific group or subset of clients.

At 710, the first client device 114(1) may send the comment or tag to a third client device 114(3) and, at 712, the third client device 114(3) may output the comment or tag in conjunction with the image data and the audio data of the session. For example, the comment or tag may be presented as part of a recording of the session including the video, audio, and text-based transcript of the session. In some cases, outputting the comment or tag may include providing an indication or icon associated with the comment or tag, such as an indicator of type of comment (e.g., question, feedback, position marker, review marker, etc.), a position within the content, the individual that posted the comment, a time stamp, etc.

At 714, the third client device 114(3) may also output an alert or notification. For example, the alert or notification may be configured to bring the comment or tag to the attention of an individual associated with the third client device 114(3). In some cases, the alert or notification may be visual-based (e.g., icon, flashing, color change on the display), audio-based (e.g., output of sound based on the comment or tag), or tactile-based (e.g., a vibration of the device), among others.

Figure 8:
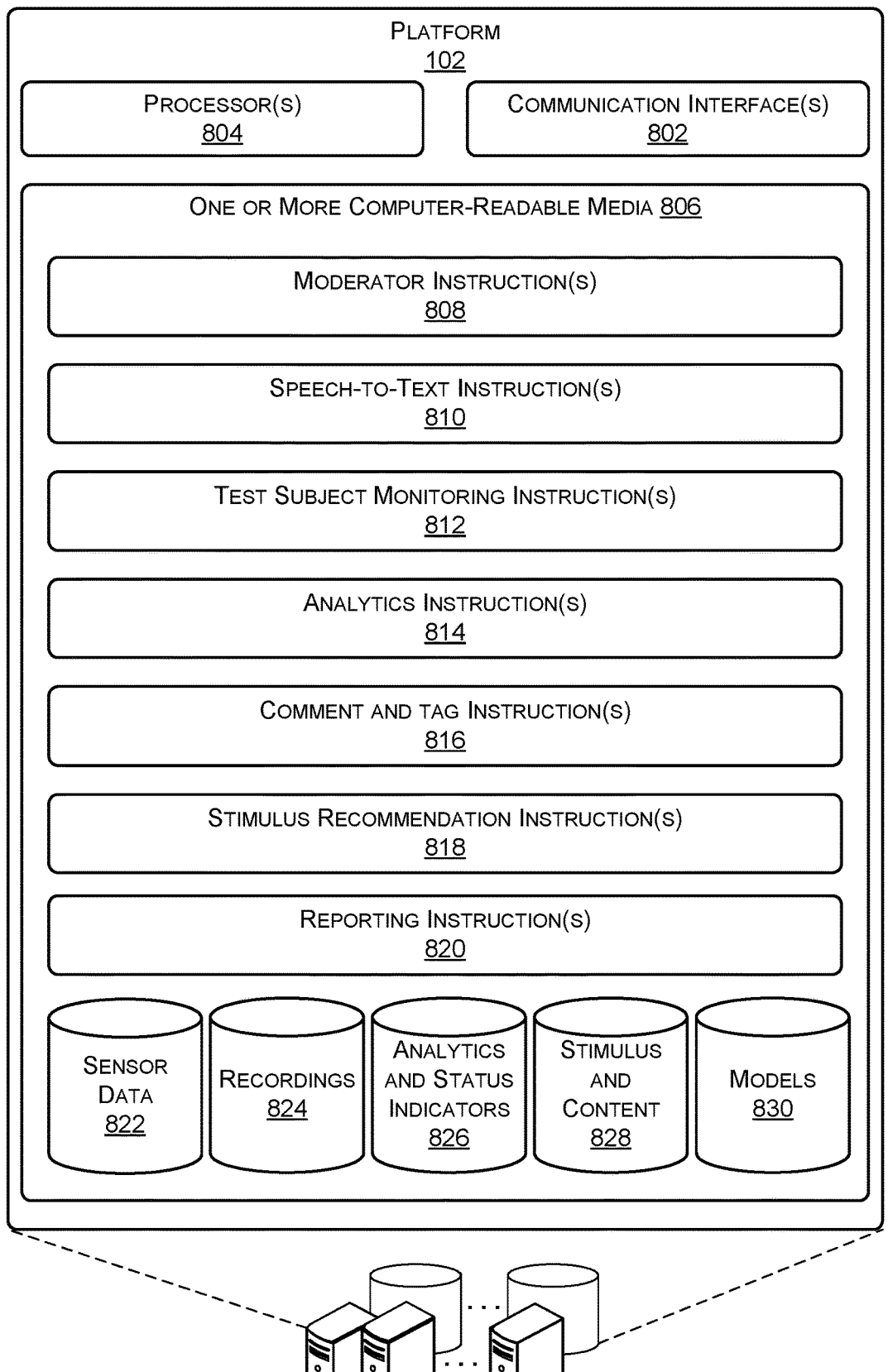
FIG. 8 illustrates an example platform for providing a virtual focus group according to some implementations.

FIG. 8 illustrates an example platform 102 for providing a virtual focus group according to some implementations. In the illustrated example, the platform 102 includes one or more communication interfaces 802 configured to facilitate communication between one or more networks, one or more system (e.g., test subject systems 106 or 108, moderator systems 112, and/or client systems 114 of FIG. 1). The communication interfaces 802 may also facilitate communication between one or more wireless access points, a master device, and/or one or more other computing devices as part of an ad-hoc or home network system. The communication interfaces 802 may support both wired and wireless connection to various networks, such as cellular networks, radio, WiFi networks, short-range or near-field networks (e.g., Bluetooth®), infrared signals, local area networks, wide area networks, the Internet, and so forth.

The platform 102 includes one or more processors 804, such as at least one or more access components, control logic circuits, central processing units, or processors, as well as one or more computer-readable media 806 to perform the function of the platform 102. Additionally, each of the processors 804 may itself comprise one or more processors or processing cores.

Depending on the configuration, the computer-readable media 806 may be an example of tangible non-transitory computer storage media and may include volatile and non-volatile memory and/or removable and non-removable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 804.

Several modules such as instructions, data stores, and so forth may be stored within the computer-readable media 806 and configured to execute on the processors 804. For example, as illustrated, the computer-readable media 806 stores moderator instructions 808, speech-to-text instructions 810, test subject monitoring instructions 812, analytics instructions 814, comment and tag instructions 816, stimulus recommendation instructions 818, reporting instructions 820 as well as other instructions, such as an operating system. The computer-readable media 806 may also be configured to store data, such as sensor data 822 collected or captured with respect to the test subjects and/or moderators, session recordings 824, analytics and status indicators 826, stimulus or content 828, and/or various models 830 for preforming the various operations and analysis of the platform 102.

The moderator instructions 808 may be configured to allow a moderator to communicate and/or provide stimuli and content 826 to the test subject via a client display and/or device. In some implementations, the moderator instructions 808 may be configured to conduct the session with the test subject as an autonomous system. For instance, the moderator instructions 808 may be configured to conduct pre-programed sessions (e.g., a series of stimuli and requests). In other instances, the moderator instructions 808 may be configured to utilize one or more machine learned model 830, neural network, and/or analytics 826 to provide to the test subject.

The speech-to-text instructions 810 may be configured to receive the audio portion of the sensor data 822 and to convert the audio data into a text-based transcript. In some cases, the speech-to-text instructions 810 may correlate or relate the text-based transcript with the audio and/or video data to generate a recording in substantially real-time, as discussed above.

The test subject monitoring instructions 812 may be configured to analyze the sensor data 822 collected from the environment associated with the test subject and to generate the status indicators 826 associated with the test subject. As discussed above, the test subject monitoring instructions 812 may utilize various machine learned models 830, neural networks, or other data analytic techniques when determining the status indicators. Additionally, the status indicators 826 may be presented to clients observing the session in various formats, such as visual (e.g., icons, colors, ratings, percentages, graphs, etc.), audio (e.g., output sounds in response to changes in mood), or text-based annotations to the recordings.

The analytics instructions 814 may be configured to analyze the sensor data 822 collected from the environment associated with the test subject with respect to multiple test sessions or test subjects and to generate analytics 826 associated with trends, common occurrences, maximum or minimum thresholds, etc. over the various sessions.

The comment and tag instructions 816 may be configured to allow clients to provide comments or tags associated with the session. For example, the comment and tag instructions 816 may allow the clients to add audio, video, or text-based information to the session recording. As discussed above, the comments and tags may be private, shared with a select group, or global. In some examples, the comment and tag instructions 816 may be configured to detect new comments associated with a current or previously conducted and recorded session and to generate alerts or notifications related to the newly detected comment or tag. In some cases, individual users may save or store filters or searches that cause the requesting individual user to receive an alert or notification upon detection of a newly added comment with respect to specified sessions.

The stimulus recommendation instructions 818 may configured to assist the moderator and/or the moderator instructions 808 with conducting a session. For example, the stimulus recommendation instructions 818 may analyze the sensor data 822 collected from the environment associated with a test subject and generate recommendations, sample questions, select stimulus or other content, that may be used to direct the session one way or another. For example, if the client specifies specific goals for the session, the recommendations, sample questions, stimulus or other content may be selected to assist in achieving the client goals.

The reporting instructions 820 may be configured to generate a summary or report of each session that may be reviewed after the session ends and include links to the actual recording 824 of the corresponding session or sessions. For example, the report generated by the platform 102 may include one or more of the transcript or dialog within a first column, the analytics within a second column, the tags within a third column, and any corresponding chat within a fourth column. In each case, the content of each column may align according to the corresponding portion of the transcript and be linked to the recording 824, such that an individual may quickly review the report and access the recording 824 for any part of the session the individual desires to watch or otherwise consume.

Figure 9:
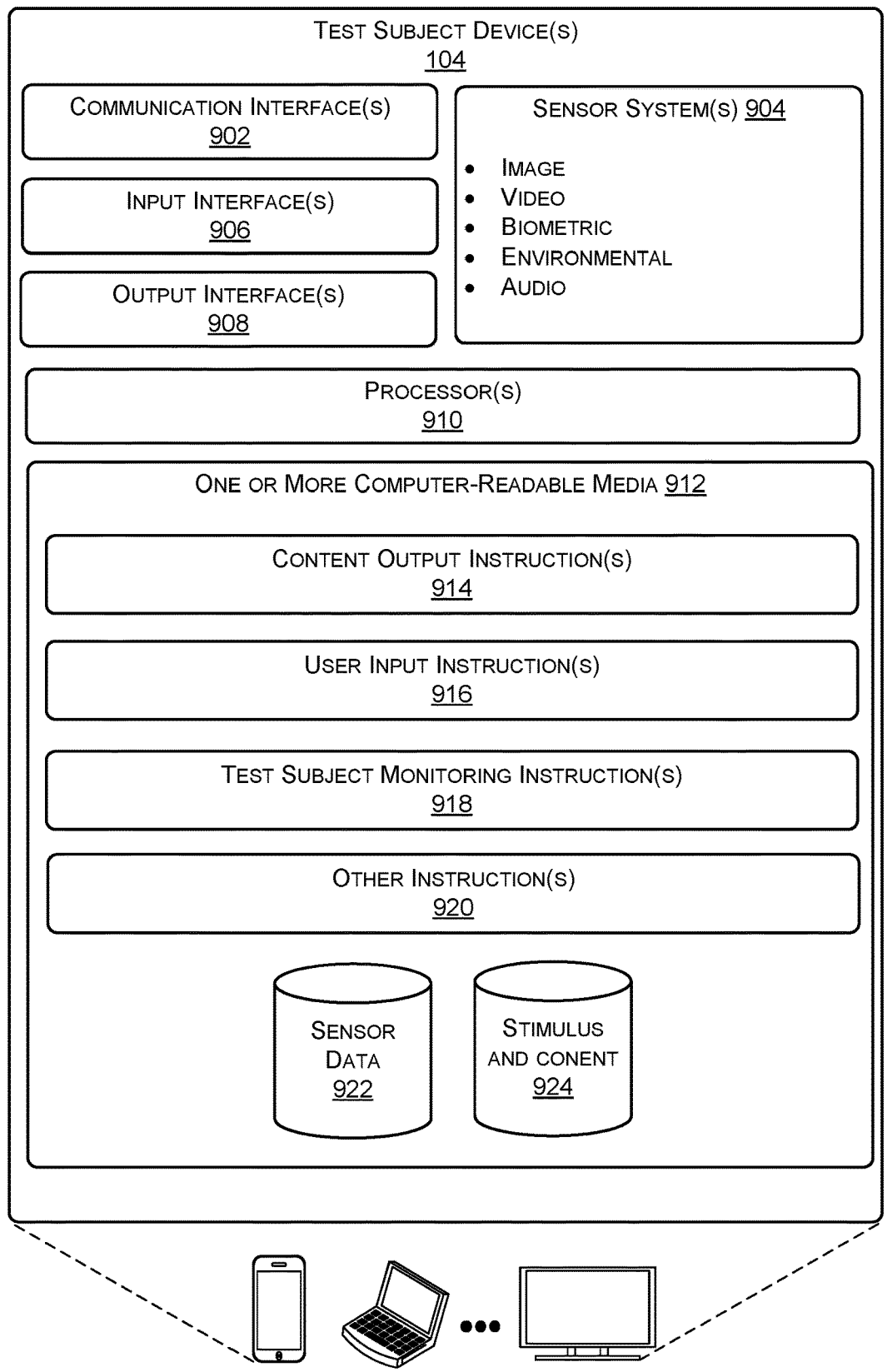
FIG. 9 illustrates an example test subject system associated with the platform of FIG. 8 according to some implementations.

FIG. 9 illustrates an example test subject system 104 associated with the platform of FIG. 8 according to some implementations. In the illustrated example, the device 104 includes one or more communication interfaces 902 configured to facilitate communication between one or more networks, one or more system (e.g., platform 102 or moderator systems 112 of FIG. 1). The communication interfaces 902 may also facilitate communication between one or more wireless access points, a master device, and/or one or more other computing devices as part of an ad-hoc or home network system. The communication interfaces 902 may support both wired and wireless connection to various networks, such as cellular networks, radio, WiFi networks, short-range or near-field networks (e.g., Bluetooth®), infrared signals, local area networks, wide area networks, the Internet, and so forth.

The device 104 may also include one or more sensors systems 904. For example, the sensor systems 904 may be configured to capture data associated with the test subject and/or the environment associated with the test subject. In some cases, the sensor systems 904 may include image data capture components, video data capture components, biometric data capture components, environmental data capture components (e.g., temperature), and audio data capture components. In general, the data captured by the sensor system 904 may be stored as sensor data 922 and provided to the platform 102 of FIG. 1 via the communication interfaces 902.

The device 104 also includes input interfaces 906 and the output interface 908 may be included to display or provide data (e.g., the stimulus and content 924) to and to receive test subject inputs. The interfaces 906 and 908 may include various systems for interacting with the device 104, such as mechanical input devices (e.g., keyboards, mice, buttons, etc.), displays, input sensors (e.g., motion, age, gender, fingerprint, facial recognition, or gesture sensors), and/or microphones for capturing natural language input such as speech. In some examples, the input interface 906 and the output interface 908 may be combined in one or more touch screen capable displays.

The device 104 includes one or more processors 910, such as at least one or more access components, control logic circuits, central processing units, or processors, as well as one or more computer-readable media 912 to perform the function associated with the virtual focus group. Additionally, each of the processors 910 may itself comprise one or more processors or processing cores.

Depending on the configuration, the computer-readable media 912 may be an example of tangible non-transitory computer storage media and may include volatile and nonvolatile memory and/or removable and non-removable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 904.

Several modules such as instruction, data stores, and so forth may be stored within the computer-readable media 912 and configured to execute on the processors 910. For example, as illustrated, the computer-readable media 912 stores content output instructions 914, user input instructions 916, test subject monitoring instructions 918, as well as other instructions 920, such as an operating system. The computer-readable media 912 may also be configured to store data, such as sensor data 922 collected or captured with respect to the test subjects and/or moderator as well as stimulus or content 924.

The content output instructions 914 may be configured to receive instruction or content 924 from the moderator system (e.g., the stimulus and requests) and in response to cause the stimulus 924 (such as image or video data) to be output by the output interfaces 908 of the device 104. The user input instructions 916 may be configured to receive user inputs via the input interface 906 and to store or send the user inputs as feedback to the platform via the communication interfaces 902.

The test subject monitoring instructions 918 may be configured to cause the sensor systems 904 to capture or collected the sensor data 922 from the environment associated with the test subject. As discussed above, the test subject monitoring instructions 918 may capture sensor data 922 associated with audio in the environment, the facial expression of the test subject, the eye movement of the test subject, various biometrics (e.g., heartrate, brain activity, etc.) of the test subject, the condition of the environment (e.g., temperature), among others.

Figure 10:
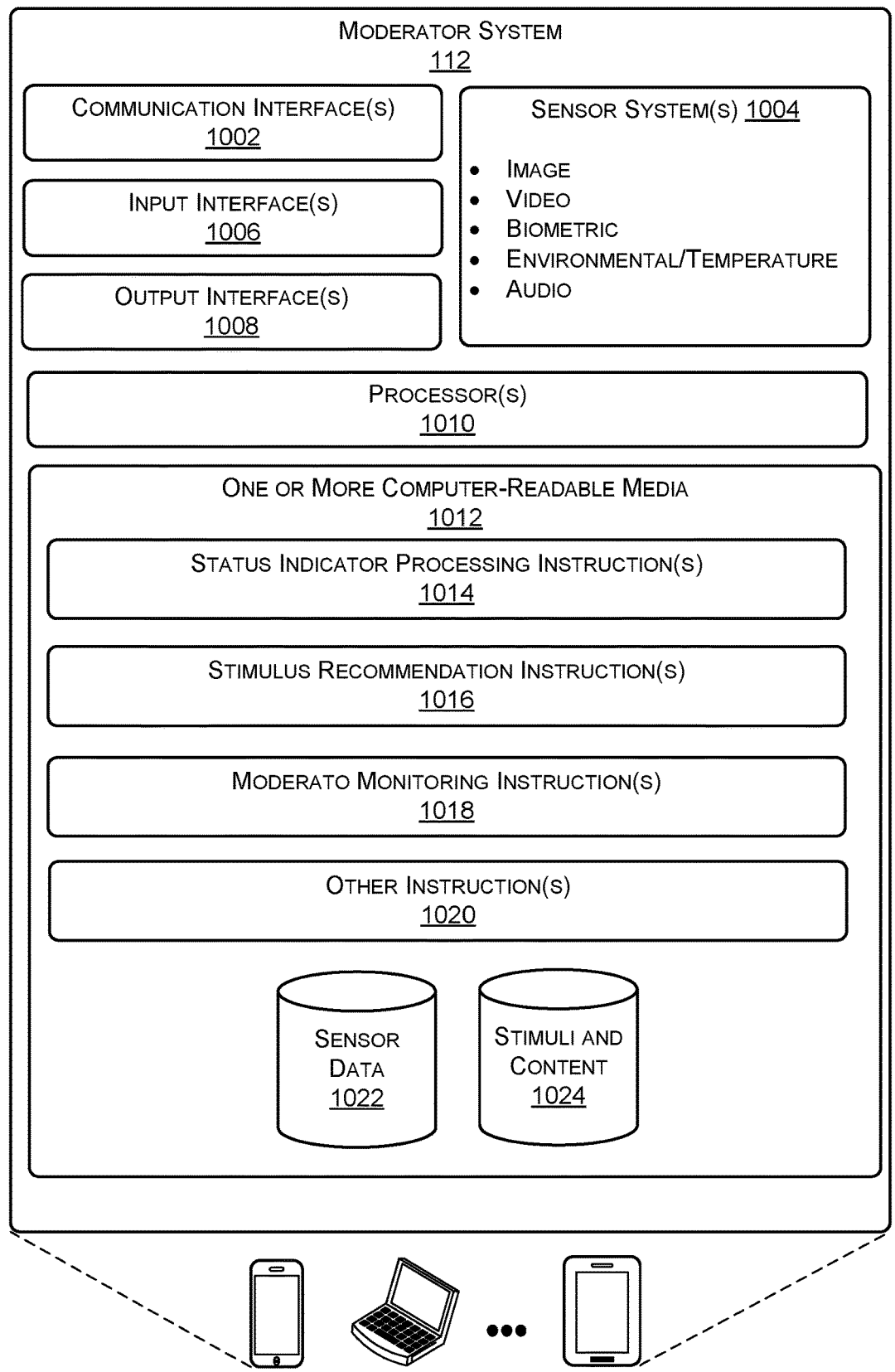
FIG. 10 illustrates an example moderator system associated with the platform of FIG. 8 according to some implementations.

FIG. 10 illustrates an example moderator system 112 associated with the platform of FIG. 8 according to some implementations. In the illustrated example, the system 112 includes one or more communication interfaces 1002 configured to facilitate communication between one or more networks, one or more system (e.g., platform 102 or test subject devices 104 or 108 of FIG. 1). The communication interfaces 1002 may also facilitate communication between one or more wireless access points, a master device, and/or one or more other computing devices as part of an ad-hoc or home network system. The communication interfaces 1002 may support both wired and wireless connection to various networks, such as cellular networks, radio, WiFi networks, short-range or near-field networks (e.g., Bluetooth®), infrared signals, local area networks, wide area networks, the Internet, and so forth.

The system 112 may also include one or more sensors systems 1004. For example, the sensor systems 1004 may be configured to capture data associated with the moderator. In some cases, the sensor systems 1004 may include image data capture components, video data capture components, biometric data capture components, environmental data capture components, and audio data capture components. In general, the data captured by the sensor system 1004 may be stored as sensor data 1022 and provided to the platform 102 of FIG. 1 via the communication interfaces 1002 to be incorporated into the session recording by the platform 102.

The system 112 also includes input interfaces 1006 and the output interface 1008 may be included to display or provide information to and to receive inputs from the moderator. The interfaces 1006 and 1008 may include various systems for interacting with the system 112, such as mechanical input devices (e.g., keyboards, mice, buttons, etc.), displays, input sensors (e.g., motion, age, gender, fingerprint, facial recognition, or gesture sensors), and/or microphones for capturing natural language input such as speech. In some examples, the input interface 1006 and the output interface 1008 may be combined in one or more touch screen capable displays.

The device 104 includes one or more processors 1010, such as at least one or more access components, control logic circuits, central processing units, or processors, as well as one or more computer-readable media 1012 to perform the function associated with the virtual focus group. Additionally, each of the processors 1010 may itself comprise one or more processors or processing cores.

Depending on the configuration, the computer-readable media 1012 may be an example of tangible non-transitory computer storage media and may include volatile and nonvolatile memory and/or removable and non-removable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 1004.

Several modules such as instruction, data stores, and so forth may be stored within the computer-readable media 1012 and configured to execute on the processors 1010. For example, as illustrated, the computer-readable media 1012 stores status indicator processing instructions 1014, stimulus recommendation instructions 1016, moderator monitoring instructions 1018, as well as other instructions 1020, such as an operating system. The computer-readable media 1012 may also be configured to store data, such as sensor data 1022 collected or captured with respect to the moderator and/or the test subject as well as stimulus or content 1024.

The status indicator processing instructions 1014 may be configured to receive a status indicator from the platform 102 and to determine how to present the status to the moderator. For example, the status indicator processing instructions 1014 may determine from the sensor data 1022 a level of concentration or involvement of the moderator with the session and determine to present the status indicator as an icon on a video feed of the test subject being displayed to the moderator. In other examples, the status indicator processing instructions 1014 may present statistical data associated with the status of the test subject, such as the heartrate, to the moderator to provide additional insight during the session.

The stimulus recommendation instructions 1016 may configured to assist the moderator with conducting a session. For example, the stimulus recommendation instructions 1016 may process the status indicators and/or analysis provided by the platform 102 and associated with a test subject to generate recommendations, sample questions, select stimulus or other content, that may be used to direct the session one way or another.

The moderator monitoring instructions 1018 may be configured to cause the sensor systems 1004 to capture or collect the sensor data 1022 from the environment associated with the moderator. The moderator monitoring instructions 1018 may capture sensor data 1022 associated with audio in the environment, the facial expression of the test subject, the eye movement of the test subject, various biometrics (e.g., heartrate, brain activity, etc.) of the test subject, the condition of the environment (e.g., temperature), and among others.

Figure 11:
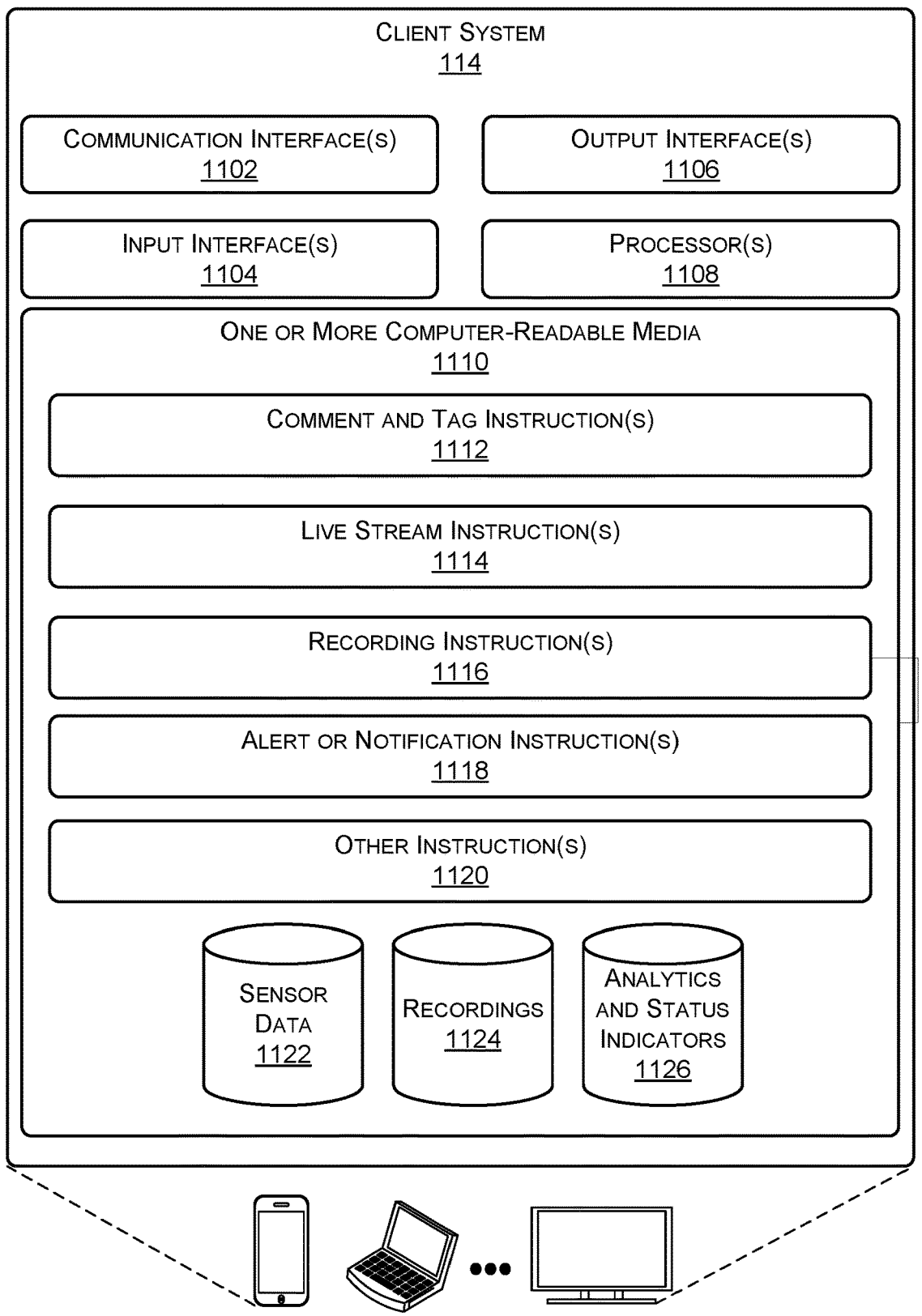
FIG. 11 illustrates an example client system associated with the platform of FIG. 8 according to some implementations.

FIG. 11 illustrates an example client system 114 associated with the platform of FIG. 8 according to some implementations. In the illustrated example, the system 114 includes one or more communication interfaces 1102 configured to facilitate communication between one or more networks, one or more system (e.g., platform 102 of FIG. 1). The communication interfaces 1102 may also facilitate communication between one or more wireless access points, a master device, and/or one or more other computing devices as part of an ad-hoc or home network system. The communication interfaces 1102 may support both wired and wireless connection to various networks, such as cellular networks, radio, WiFi networks, short-range or near-field networks (e.g., Bluetooth®), infrared signals, local area networks, wide area networks, the Internet, and so forth.

The system 114 also includes input interfaces 1104 and the output interface 1106 may be included to display or provide information to and to receive inputs from the moderator. The interfaces 1104 and 1106 may include various systems for interacting with the system 114, such as mechanical input devices (e.g., keyboards, mice, buttons, etc.), displays, input sensors (e.g., motion, age, gender, fingerprint, facial recognition, or gesture sensors), and/or microphones for capturing natural language input such as speech. In some examples, the input interface 1106 and the output interface 1108 may be combined in one or more touch screen capable displays.

The system 114 includes one or more processors 1108, such as at least one or more access components, control logic circuits, central processing units, or processors, as well as one or more computer-readable media 1110 to perform the function associated with the virtual focus group. Additionally, each of the processors 1108 may itself comprise one or more processors or processing cores.

Depending on the configuration, the computer-readable media 1110 may be an example of tangible non-transitory computer storage media and may include volatile and non-volatile memory and/or removable and non-removable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 1108.

Several modules such as instruction, data stores, and so forth may be stored within the computer-readable media 1110 and configured to execute on the processors 1108. For example, as illustrated, the computer-readable media 1110 stores comment and tag instructions 1112, live stream instructions 1114, recording instructions 1116, alert or notification instructions 1118, as well as other instructions 1120, such as an operating system. The computer-readable media 1110 may also be configured to store data, such as sensor data 1122 collected or captured with respect to the moderator and/or the test subject.

The comment and tag instructions 1112 may allow a user (e.g., an individual client) to insert comments and tags to the recording of the session. For example, the comment may be a question for other clients, personal notes, feedback for other clients, etc. The tags may include various prepopulated bookmarks, tabs, etc. that may be applied to portions or segments of the session. For example, the tag may indicate an intent to review at a later time and be assigned a particular color. In some cases, tags may include underlining, highlighting, circling, etc. of text within the transcript of the session.

The live stream instructions 1114 may be configured to cause the audio and video data captured with respect to one or more test subject and/or a moderator to be displayed via the output interfaces as the session is progressing.

The recording instructions 1116 may be configured to cause a recording of a session to be displayed by the output interfaces 1106 either as session is live or at a time subsequent to the session. In some examples, the recording may be presented on a first output interface 1106 (or device) and the audio and video data may be presented on a second output interface 1106 (or device). In some cases, the recording may include a transcript of the session linked to the video and audio such that the transcript is searchable via various types of text-based searches and that upon selection of a portion of the transcript the corresponding video and audio data may be presented to the client via the output interface 1106.

In some examples, the recording instructions 1116 may also include one or more editor modes available to the clients via the client systems. For example, the recording instructions 1116 may allow for a clip extractor that allows one or more clients to extract or automatically flag a predetermined period of time (such as 30 seconds) around search terms, types of tags, particular tags, designated comments, etc. In some cases, the predetermined period of time may be a first predetermined period prior to the search term and a second predetermined period after the search term (e.g., 15 seconds prior to the search term and 15 seconds following the search term may be extracted to form a 30 second clip). The recording instructions 1116 may also include a second more detailed editor mode that may operate in a manner similar to a video editor.

The alert or notification instructions 1118 may be configured to generate an alert or notification in response to detecting a new comment or tag within a session or in response to receiving a notification from the platform 102 of FIG. 1. In some cases, the types of alerts and/or notification may be set by the user of the client system 114 or by the type of device of the system 114. In some cases, the user may be able to set or the alerts to issue in response to particular clients adding comments, particular content of a session being tagged or commented upon, and/or particular user's making a comment or tagging content of a session.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

Example Clauses A. A system comprising: one or more communication interfaces; one or more processors; and computer-readable storage media storing computer-executable instructions, which when executed by the one or more processors cause the one or more processors to: communicatively couple, via the one or more communication interfaces a moderator system to a test subject device during a session; receive test subject image data, test subject audio data, and test subject sensor data from the test subject device, the test subject image data, the test subject audio data, and the test subject sensor data associated with the session; receive moderator image data and moderator audio data from a moderator system, the moderator image data and the moderator audio data associated with the session; generate a live stream based at least in part on the test subject image data, the test subject audio data, the moderator image data, and the moderator audio data; convert the test subject audio data and the moderator audio data into a first text-based transcript; generate a session recording based at least in part on the first data including the test subject image data, the test subject audio data, the moderator image data, and the moderator audio data, and the first text-based transcript; send, via the one or more communication interfaces, the live stream to a first client device associated with a first client user; send, via the one or more communication interfaces and substantially simultaneously with the live stream, the session recording to a second client device associated with the first client user.

B. The system of claim A, wherein the test subject sensor data is biometric data associated with the test subject and the computer-readable storage media stores additional computer-executable instructions, which when executed by the one or more processors cause the one or more processors to: analyze the biometric data to determine a status indictor representative of a mood of the test subject; and sending, the status indicator, to the moderator system.

C. The system of claim B, wherein the computer-readable storage media stores additional computer-executable instructions, which when executed by the one or more processors cause the one or more processors to send, via the one or more communication interfaces and substantially simultaneously with the live stream, the status indicators to the second client device associated with the first client user.

D. The system of claim B, wherein the computer-readable storage media stores additional computer-executable instructions, which when executed by the one or more processors cause the one or more processors to: associate the status indictor with a portion of the test subject image data representative of the test subject; and wherein the status indicator is at least one of an icon or a color and the status indictor is incorporated into the live stream.

E. The system of claim A, wherein the computer-readable storage media stores additional computer-executable instructions, which when executed by the one or more processors cause the one or more processors to: receive feedback associated with test subject responses from the test subject device; and wherein the session recording is based at least in part on the feedback.

F. The system of claim A, wherein the computer-readable storage media stores additional computer-executable instructions, which when executed by the one or more processors cause the one or more processors to: identifying at least one trend based at least in part on the test subject image data, the test subject audio data, the moderator image data, and the moderator audio data, the first text-based transcript, and another session recording associated with a second test subject; and associating the at least one trend with the session recording prior to sending to the second client device.

G. The system of claim A, wherein the computer-readable storage media stores additional computer-executable instructions, which when executed by the one or more processors cause the one or more processors to: receive a search request from the second client device; identify from the text-based transcript a portion of the text-based transcript meeting or exceeding a criterion of the search request; and sending the portion of the text-based transcript to the second client device.

H. The system of claim G, wherein the computer-readable storage media stores additional computer-executable instructions, which when executed by the one or more processors cause the one or more processors to: identify from a second text-based transcript of a second test session, a portion of the second text-based transcript meeting or exceeding a criterion of the search request; and sending the portion of the second text-based transcript to the second client device with the portion of the first text-based transcript.

I. A method comprising: receive test subject image data, test subject audio data, and test subject biometric data from the test subject device, the test subject image data, the test subject audio data, and the test subject biometric data associated with a session between a moderator and a test subject; receive moderator image data and moderator audio data from a moderator device, the moderator image data and the moderator audio data associated with the session; generate a live stream based at least in part on the test subject image data, the test subject audio data, the moderator image data, and the moderator audio data; convert the test subject audio data and the moderator audio data into a first text-based transcript; generate a status indicator associated with the test subject based at least in part on the biometric data; generate a session recording based at least in part on the first data including the test subject image data, the test subject audio data, the moderator image data, and the moderator audio data, the first text-based transcript, and the status indicators; send the live stream to a first client device associated with a first client user and the moderator system; send, substantially simultaneously with the live stream, the status indicators to the moderator system; and send, substantially simultaneously with the live stream, the session recording to a second client device associated with the first client user.

J. The method of claim I, further comprising: receiving at least one stimulus to present on a display of the test subject device from the moderator system; sending the at least one stimulus to the test subject device; determining from the biometric data or the image data a portion of the stimulus that the test subject is viewing; and wherein the status indictor includes the portion of the stimulus.

K. The method of claim I, wherein receiving the at least one stimulus includes selecting the at least one stimulus from a plurality of stimulus based at least in part on the test subject image data, test subject audio data, and test subject biometric data.

L. The method of claim I, wherein receiving the at least one stimulus includes: selecting one or more stimulus from a plurality of stimulus based at least in part on the test subject image data, test subject audio data, and test subject biometric data; sending the one or more stimulus to the moderator system; and receiving the at least one stimulus from the moderator system.

M. The method of claim I, further comprising: identifying at least one trend based at least in part on the test subject image data, the test subject audio data, the biometric data, the first text-based transcript, and another session recording associated with a second test subject; and associating the at least one trend with the session recording prior to sending to the second client device.

N. The method of claim I, wherein the status indicators are configured to display with the image data such that the status indicators are adjacent to or over a portion of the image data representing the test subject.

O. One or more non-transitory computer-readable media having computer-executable instructions that, when executed by one or more processors, cause the one or more processors to perform operations comprising: providing a first video and audio stream from a test subject device to a moderator system, the first video and audio stream including data representative of a test subject; providing a second video and audio stream from the moderator system to the test subject device; providing the first video and audio stream and the second video to a first client device, the first client device associated with a first client user; generating a text-based transcript based at least in part on the first video and audio stream and the second video and audio stream; generating a status indictor associated with a mood of the test subject based at least in part on the first video and audio stream and biometric data associated with the test subject; generate a session recording including the first video and audio stream, the second video and audio stream, the text-based transcript, and the status indictor; providing the session recording to a second client device, the second client device associated with the first client user and different than the first client device; providing the session recording to a third client device, the third client device associated with a second client user and different than the first client device and the second client device; receiving a comment associated with the session recoding from the third client device; and causing an alert to be output by the second client device in response to reaching the comment, the alert associated with the comment and the session recording.

P. The one or more computer-readable media as recited in claim O, wherein the comment includes an indication of at least a portion of the session recording.

Q. The one or more computer-readable media as recited in claim P, wherein causing the alert to be output by the second client device includes at least one of determining the second user is associated with a set of user or that the portion of the session recording corresponds to a portion of the session recording tagged by the first client user.

R. The one or more computer-readable media as recited in claim O, having computer-executable instructions that, when executed by the one or more processors, cause the one or more processors to perform operations comprising providing the status indictors to the moderator system.

S. The one or more computer-readable media as recited in claim O, having computer-executable instructions that, when executed by the one or more processors, cause the one or more processors to perform operations comprising: identifying at least one trend based at least in part on the text-based transcript; and providing the trend to the second client device and the third client device.

T. The one or more computer-readable media as recited in claim O, wherein the biometric data includes brain activity data and heartrate data.

What is claimed is:

1. A system comprising:
one or more communication interfaces;
one or more processors; and
computer-readable storage media storing computer-executable instructions, which when executed by the one or more processors cause the one or more processors to:
communicatively couple, via the one or more communication interfaces a moderator system to a test subject device during a session;
receive test subject image data, test subject audio data, and test subject sensor data from the test subject device, the test subject image data, the test subject audio data, and the test subject sensor data associated with the session;
receive moderator image data and moderator audio data from a moderator system, the moderator image data and the moderator audio data associated with the session;
generate a live stream based at least in part on the test subject image data, the test subject audio data, the moderator image data, and the moderator audio data;
convert the test subject audio data and the moderator audio data into a first text-based transcript;
generate a session recording based at least in part on the first data including the test subject image data, the test subject audio data, the moderator image data, and the moderator audio data, and the first text-based transcript;
send, via the one or more communication interfaces, the live stream to a first client device associated with a first client user;
identify at least one trend based at least in part on the test subject image data, the test subject audio data, the moderator image data, and the moderator audio data, the first text-based transcript, and another session recording associated with a second test subject;
associate the at least one trend with the session recording prior to sending to the second client device; and
send, via the one or more communication interfaces and substantially simultaneously with the live stream, the session recording to a second client device associated with the first client user.

2. The system as recited in claim 1, wherein the test subject sensor data is biometric data associated with the test subject and the computer-readable storage media stores additional computer-executable instructions, which when executed by the one or more processors cause the one or more processors to:
analyze the biometric data to determine a status indictor representative of a mood of the test subject; and
sending, the status indicator, to the moderator system.

3. The system as recited in claim 2, wherein the computer-readable storage media stores additional computer-executable instructions, which when executed by the one or more processors cause the one or more processors to send, via the one or more communication interfaces and substantially simultaneously with the live stream, the status indicators to the second client device associated with the first client user.

4. The system as recited in claim 2, wherein the computer-readable storage media stores additional computer-executable instructions, which when executed by the one or more processors cause the one or more processors to:
associate the status indictor with a portion of the test subject image data representative of the test subject; and
wherein the status indicator is at least one of an icon or a color and the status indictor is incorporated into the live stream.

5. The system as recited in claim 2, wherein the biometric data includes brain activity data and heartrate data.

6. The system as recited in claim 1, wherein the computer-readable storage media stores additional computer-executable instructions, which when executed by the one or more processors cause the one or more processors to:
receive feedback associated with test subject responses from the test subject device; and
wherein the session recording is based at least in part on the feedback.

7. The system as recited in claim 1, wherein the computer-readable storage media stores additional computer-executable instructions, which when executed by the one or more processors cause the one or more processors to:
receive a search request from the second client device;
identify from the text-based transcript a portion of the text-based transcript meeting or exceeding a criterion of the search request; and
sending the portion of the text-based transcript to the second client device.

8. The system as recited in claim 7, wherein the computer-readable storage media stores additional computer-executable instructions, which when executed by the one or more processors cause the one or more processors to:
identify from a second text-based transcript of a second test session, a portion of the second text-based transcript meeting or exceeding a criterion of the search request; and
sending the portion of the second text-based transcript to the second client device with the portion of the first text-based transcript.

9. The system as recited in claim 1, wherein the computer-readable storage media stores additional computer-executable instructions, which when executed by the one or more processors cause the one or more processors to:
receiving a comment associated with the session; and
sending an alert associated with the comment to the moderator system.

10. A method comprising:
receive test subject image data, test subject audio data, and test subject biometric data from the test subject device, the test subject image data, the test subject audio data, and the test subject biometric data associated with a session between a moderator and a test subject;
receive moderator image data and moderator audio data from a moderator device, the moderator image data and the moderator audio data associated with the session;
generate a live stream based at least in part on the test subject image data, the test subject audio data, the moderator image data, and the moderator audio data;
convert the test subject audio data and the moderator audio data into a first text-based transcript;
generate a status indicator associated with the test subject based at least in part on the biometric data;
generate a session recording based at least in part on the first data including the test subject image data, the test subject audio data, the moderator image data, and the moderator audio data, the first text-based transcript, and the status indicators;
send the live stream to a first client device associated with a first client user and the moderator system;
send, substantially simultaneously with the live stream, the status indicators to the moderator system;
identifying at least one trend based at least in part on the test subject image data, the test subject audio data, the biometric data, the first text-based transcript, and another session recording associated with a second test subject; and
associating the at least one trend with the session recording prior to sending to the second client device; and
send, substantially simultaneously with the live stream, the session recording to a second client device associated with the first client user.

11. The method as recited in claim 10, further comprising:
receiving at least one stimulus to present on a display of the test subject device from the moderator system;
sending the at least one stimulus to the test subject device;
determining from the biometric data or the image data a portion of the stimulus that the test subject is viewing; and
wherein the status indicator includes the portion of the stimulus.

12. The method as recited in claim 11, wherein receiving the at least one stimulus includes selecting the at least one stimulus from a plurality of stimulus based at least in part on the test subject image data, test subject audio data, and test subject biometric data.

13. The method as recited in claim 11, wherein receiving the at least one stimulus includes:
selecting one or more stimulus from a plurality of stimulus based at least in part on the test subject image data, test subject audio data, and test subject biometric data;
sending the one or more stimulus to the moderator system; and
receiving the at least one stimulus from the moderator system.

14. The method as recited in claim 10, wherein the status indicators are configured to display with the image data such that the status indicators are adjacent to or over a portion of the image data representing the test subject.

15. The method as recited in claim 10, wherein the biometric data includes brain activity data and heartrate data.

16. One or more non-transitory computer-readable media having computer-executable instructions that, when executed by one or more processors, cause the one or more processors to perform operations comprising:
  providing a first video and audio stream from a test subject device to a moderator system, the first video and audio stream including data representative of a test subject;
  providing a second video and audio stream from the moderator system to the test subject device;
  providing the first video and audio stream and the second video to a first client device, the first client device associated with a first client user;
  generating a text-based transcript based at least in part on the first video and audio stream and the second video and audio stream;
  generating a status indictor associated with a mood of the test subject based at least in part on the first video and audio stream and biometric data associated with the test subject;
  generate a session recording including the first video and audio stream, the second video and audio stream, the text-based transcript, and the status indictor;
  providing the session recording to a second client device, the second client device associated with the first client user and different than the first client device;
  providing the session recording to a third client device, the third client device associated with a second client user and different than the first client device and the second client device;
  receiving a comment associated with the session recoding from the third client device; and
  causing an alert to be output by the second client device in response to reaching the comment, the alert associated with the comment and the session recording; and
  wherein causing the alert to be output by the second client device includes at least one of determining the second user is associated with a set of user or that the portion of the session recording corresponds to a portion of the session recording tagged by the first client user.

17. The one or more computer-readable media as recited in claim 16, wherein the comment includes an indication of at least a portion of the session recording.

18. The one or more computer-readable media as recited in claim 16, having computer-executable instructions that, when executed by the one or more processors, cause the one or more processors to perform operations comprising providing the status indictors to the moderator system.

19. The one or more computer-readable media as recited in claim 16, having computer-executable instructions that, when executed by the one or more processors, cause the one or more processors to perform operations comprising:
  identifying at least one trend based at least in part on the text-based transcript; and
  providing the trend to the second client device and the third client device.

20. The one or more computer-readable media as recited in claim 16, wherein the biometric data includes brain activity data and heartrate data.

* * * * *